US012681010B2

(12) United States Patent
Heikenfeld

(10) Patent No.: US 12,681,010 B2
(45) Date of Patent: Jul. 14, 2026

(54) CONTINUOUS SENSING WITH ADAPTERS AND APTAMERS

(71) Applicant: University of Cincinnati, Cincinnati, OH (US)

(72) Inventor: Jason Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 753 days.

(21) Appl. No.: 18/246,040

(22) PCT Filed: Sep. 24, 2021

(86) PCT No.: PCT/US2021/051879
§ 371 (c)(1),
(2) Date: Mar. 21, 2023

(87) PCT Pub. No.: WO2022/066992
PCT Pub. Date: Mar. 31, 2022

(65) Prior Publication Data
US 2023/0358736 A1     Nov. 9, 2023

Related U.S. Application Data

(60) Provisional application No. 63/197,674, filed on Jun. 7, 2021, provisional application No. 63/150,677, filed on Feb. 18, 2021, provisional application No. 63/150,667, filed on Feb. 18, 2021, provisional application No. 63/150,865, filed on Feb. 18, 2021, provisional application No. 63/150,944, filed on Feb. 18, 2021, provisional application No. 63/150,986, filed on Feb. 18, 2021, provisional application No. 63/150,856, filed on Feb. 18, 2021, provisional application No. 63/150,894, filed on Feb. 18, 2021, provisional application No. 63/150,712, filed on Feb. 18, 2021, provisional application No. 63/150,953, filed on Feb. 18, 2021, provisional application No. 63/136,262, filed on Jan. 12, 2021, provisional application No. 63/122,076, filed on Dec. 7, 2020, provisional application No. 63/122,071, filed on Dec. 7, 2020, provisional application No. 63/085,484, filed on Sep. 30, 2020, provisional application No. 63/083,029, filed on Sep. 24, 2020, provisional application No. 63/082,834, filed on Sep. 24, 2020, provisional application No. 63/082,999, filed on Sep. 24, 2020.

(51) Int. Cl.
| | |
|---|---|
| *C12N 15/115* | (2010.01) |
| *G01N 27/327* | (2006.01) |
| *G01N 27/416* | (2006.01) |
| *G01N 27/48* | (2006.01) |
| *G01N 33/53* | (2006.01) |
| *G01N 33/542* | (2006.01) |
| *G01N 33/543* | (2006.01) |
| *G01N 33/58* | (2006.01) |
| *G01N 33/74* | (2006.01) |
| *A61B 5/145* | (2006.01) |
| *A61B 5/1468* | (2006.01) |

(52) U.S. Cl.
CPC ......... *G01N 33/542* (2013.01); *C12N 15/115* (2013.01); *G01N 27/3276* (2013.01); *G01N 27/3277* (2013.01); *G01N 27/3278* (2013.01); *G01N 27/4161* (2013.01); *G01N 27/48* (2013.01); *G01N 33/5306* (2013.01); *G01N 33/5308* (2013.01); *G01N 33/5438* (2013.01); *G01N 33/582* (2013.01); *G01N 33/743* (2013.01); *A61B 5/14546* (2013.01); *A61B 5/1468* (2013.01); *C12N 2310/16* (2013.01)

(58) Field of Classification Search
None
See application file for complete search history.

(56) References Cited

U.S. PATENT DOCUMENTS

| | | |
|---|---|---|
| 6,927,070 B1 | 8/2005 | Bayley et al. |
| 2005/0006253 A1 | 1/2005 | Samproni |
| | (Continued) | |

FOREIGN PATENT DOCUMENTS

| | | |
|---|---|---|
| CN | 105711017 A | 6/2016 |
| KR | 20060080097 A | 7/2006 |
| | (Continued) | |

OTHER PUBLICATIONS

Hall et al (Current Protocols in Molecular Biology section 24.3.1 to 24.3.27) (Year: 2009).*

(Continued)

*Primary Examiner* — Christopher M Gross

(74) *Attorney, Agent, or Firm* — Wood Herron & Evans LLP

(57) ABSTRACT

A device and method for detecting the presence of, or measuring the concentration of amount of, at least one analyte in a sample fluid. The device includes a sensor fluid (18), a plurality of adapter molecules (980) in the sensor fluid that are capable of binding to an analyte, a plurality of aptamers (970) in the sensor fluid that are capable of binding to the analyte when analyte is bound to one or more adapter molecules of the plurality of adapter molecules, at least one membrane (936) in communication with the sensor fluid, and at least one detection component that is capable of detecting the binding of analyte by one or more of the plurality of aptamers. The membrane is permeable to the analyte but impermeable to the adapter molecule.

47 Claims, 9 Drawing Sheets

(56) References Cited

U.S. PATENT DOCUMENTS

| | | |
|---|---|---|
| 2005/0131386 A1 | 6/2005 | Freeman et al. |
| 2005/0154272 A1 | 7/2005 | Dirac et al. |
| 2005/0176017 A1 | 8/2005 | Breaker |
| 2005/0214759 A1 | 9/2005 | Wlassof et al. |
| 2005/0230270 A1 | 10/2005 | Ren et al. |
| 2008/0027302 A1 | 1/2008 | Buse et al. |
| 2008/0176334 A1 | 7/2008 | Baranov et al. |
| 2008/0293160 A1 | 11/2008 | Sen et al. |
| 2009/0023157 A1 | 1/2009 | Lee et al. |
| 2010/0173347 A1 | 7/2010 | Brook et al. |
| 2011/0136099 A1 | 6/2011 | Schneider et al. |
| 2013/0220832 A1 | 8/2013 | O'Connor et al. |
| 2013/0307093 A1 | 11/2013 | Bikumandla |
| 2013/0337368 A1 | 12/2013 | Doyen et al. |
| 2014/0234982 A1 | 8/2014 | Paterson et al. |
| 2015/0182932 A1 | 7/2015 | Trau |
| 2016/0245774 A1 | 8/2016 | Tayebi et al. |
| 2017/0014511 A1 | 1/2017 | Vitaliano et al. |
| 2017/0325724 A1 | 11/2017 | Wang et al. |
| 2018/0104399 A1 | 4/2018 | Dowell |
| 2018/0117624 A1 | 5/2018 | Han et al. |
| 2018/0199866 A1 | 7/2018 | Heikenfeld |
| 2018/0282804 A1 | 10/2018 | Hindson et al. |
| 2018/0353748 A1 | 12/2018 | Heikenfeld et al. |
| 2019/0053743 A1 | 2/2019 | Simpson et al. |
| 2019/0169684 A1 | 6/2019 | Oldham et al. |
| 2019/0209063 A1 | 7/2019 | Plaxco et al. |
| 2019/0230766 A1 | 7/2019 | Sugahara et al. |
| 2019/0276828 A1 | 9/2019 | Wei et al. |
| 2019/0383770 A1 | 12/2019 | Choi et al. |
| 2020/0041501 A1 | 2/2020 | Konry et al. |
| 2020/0196925 A1 | 6/2020 | Lin et al. |
| 2020/0277664 A1 | 9/2020 | Frenz |
| 2022/0095961 A1* | 3/2022 | White ................. A61B 5/1468 |

FOREIGN PATENT DOCUMENTS

| | | | |
|---|---|---|---|
| WO | 0070329 A1 | 11/2000 | |
| WO | 2017164982 A1 | 9/2017 | |
| WO | 2017189122 A1 | 11/2017 | |
| WO | 2019126620 A1 | 6/2019 | |
| WO | 2019213520 A1 | 11/2019 | |
| WO | 2019232618 A1 | 12/2019 | |
| WO | 2020069185 A1 | 4/2020 | |
| WO | 2020146002 A1 | 7/2020 | |
| WO | 2020146045 A1 | 7/2020 | |
| WO | 2021030517 A1 | 2/2021 | |

OTHER PUBLICATIONS

Shaver. "Alkanethiol Monolayer End Groups Affect the Long-Term Operational Stability and Signaling of Electrochemical, Aptamer-Based Sensors in Biological Fluids" 11214-11223. ACS: Applied Materials and Interfaces. Feb. 2020; Abstract; pp. 11215, 11216, 11219, 11221; Figure 1.

Zhang. "CuSO4/H202-Triggered Polydopamine/Poly(sulfobetaine methacrylate) Coatings for Antifouling Membrane Surfaces" 1210-1216. Langmuir. Jan. 2017; Abstract.

Zhao. "Using Two-Stage Chemical Amplification To Determine the Density of Defects in Self-Assembled Monolayers of Alkanethiolates on Gold" 3257-3264. ACS Journal of Surfaces and Colloids. Jan. 1996; Abstract; p. 3257.

Cerruti. "Poly(ethylene glycol) Monolayer Formation and Stability on Gold and Silicon Nitride Substrates" 10646=10653. Langmuir. Aug. 2008; Abstract.

Koo. "Porous Ion Exchange Polymer Matrix for Ultrasmall Au Nanoparticle-Decorated Carbon Nanotube Chemiresistors" 5413-5420. Chemistry of Materials. 2019; p. 6.

Suarez-Martinez. "Probing the interaction between gold nanoparticles and oxygen functionalized carbon nanotubes" 1549-1554. Elsevier. Feb. 2009; Entire Document.

International Search Report and Written Opinion in Intl. Patent Application No. PCT/US2022/044512, dated Mar. 15, 2023, 18 pgs.

International Search Report and Written Opinion in Intl. Patent Application No. PCT/US2022/044512, dated Dec. 13, 2021, 10 pgs.

International Search Report and Written Opinion in International Patent Application No. PCT/US2021/051857, mailed Jan. 6, 2022, 14 pgs.

International Search Report and Written Opinion in International Patent Application No. PCT/US2021/051862, mailed Jan. 5, 2022, 13 pgs.

International Search Report and Written Opinion in International Patent Application No. PCT/US2021/051879, mailed Dec. 13, 2021, 10 pgs.

International Search Report and Written Opinion in International Patent Application No. PCT/US2021/051919, mailed Dec. 27, 2021, 12 pgs.

International Search Report and Written Opinion, issued in corresponding PCT Application No. PCT/US2021/051859, dated Jan. 6, 2022, 15 pgs.

International Search Report and Written Opinion in International Patent Application No. PCT/US2021/051855, dated Jan. 5, 2022, 15 pgs.

International Search Report and Written Opinion in International Patent Application No. PCT/US2021/051967, dated Feb. 10, 2022, 10 pgs.

European Supplementary Search Report in European Patent Application No. 21873522.3, dated Feb. 23, 2024, 12 pgs.

European Supplementary Search Report in European Patent Application No. 21873479.6, dated Mar. 7, 2024, 14 pgs.

Supplementary European Search Report in European Patent Application No. 21873476.2, dated Feb. 23, 2024, 14 pgs.

PCT Office, International Preliminary Report on Patentability in International Patent Application No. PCT/US/2021/051919, dated Mar. 28, 2023, 9 pgs.

PCT Office, International Preliminary Report on Patentability issued in International Patent Application No. PCT/US2021/051859, dated Mar. 28, 2023, 12 pgs.

PCT Office, International Preliminary Report on Patentability in International Patent Application No. PCT/US2021/051855, dated Mar. 28, 2023, 12 pgs.

PCT Office, International Preliminary Report on Patentability issued in International Patent Application No. PCT/US2021/051967, dated Mar. 28, 2023, 9 pgs.

PCT Office, International Preliminary Report on Patentability in International Patent Application No. PCT/US2021/051862, dated Mar. 28, 2023, 8 pgs.

PCT Office, International Preliminary Report on Patentability in Internation Patent Application No. PCT/US2021/051857, dated Mar. 28, 2023, 10 pgs.

PCT Office, International Preliminary Report on Patentability in International Patent Application No. PCT/US2021/051879, issued Mar. 28, 2023, 7 pgs.

European Patent Office, Extended European Search Report issued in European Patent Application No. 21873484.6, dated Jan. 17, 2024, 11 pgs.

* cited by examiner

CONTINUOUS SENSING WITH ADAPTERS AND APTAMERS

CROSS-REFERENCE TO RELATED APPLICATIONS

This application claims the benefit of the filing date of U.S. Patent Application Ser. No. 63/082,834, filed on Sep. 24, 2020; claims the benefit of the filing date of U.S. Patent Application Ser. No. 63/082,999, filed on Sep. 24, 2020; claims the benefit of the filing date of U.S. Patent Application Ser. No. 63/083,029, filed on Sep. 24, 2020; claims the benefit of the filing date of U.S. Patent Application Ser. No. 63/085,484, filed on Sep. 30, 2020; claims the benefit of the filing date of U.S. Patent Application Ser. No. 63/122,071, filed on Dec. 7, 2020; claims the benefit of the filing date of U.S. Patent Application Ser. No. 63/122,076, filed on Dec. 7, 2020; claims the benefit of the filing date of U.S. Patent Application Ser. No. 63/136,262, filed on Jan. 12, 2021; claims the benefit of the filing date of U.S. Patent Application Ser. No. 63/150,667, filed on Feb. 18, 2021; claims the benefit of the filing date of U.S. Patent Application Ser. No. 63/150,677, filed on Feb. 18, 2021; claims the benefit of the filing date of U.S. Patent Application Ser. No. 63/150,712, filed on Feb. 18, 2021; claims the benefit of the filing date of U.S. Patent Application Ser. No. 63/150,856, filed on Feb. 18, 2021; claims the benefit of the filing date of U.S. Patent Application Ser. No. 63/150,865, filed on Feb. 18, 2021; claims the benefit of the filing date of U.S. Patent Application Ser. No. 63/150,894, filed on Feb. 18, 2021; claims the benefit of the filing date of U.S. Patent Application Ser. No. 63/150,944, filed on Feb. 18, 2021; claims the benefit of the filing date of U.S. Patent Application Ser. No. 63/150,953, filed on Feb. 18, 2021; claims the benefit of the filing date of U.S. Patent Application Ser. No. 63/150,986, filed on Feb. 18, 2021; and claims the benefit of the filing date of U.S. Patent Application Ser. No. 63/197,674, filed on Jun. 7, 2021, the disclosures of each of which are incorporated by reference herein in their entireties.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Interstitial fluid contains many of the same analytes as blood and often at comparable concentrations. As a result, interstitial fluid presents an alternative biofluid to blood for detection of analytes such as glucose for diabetes monitoring. Commonly employed practices for continuous monitoring of glucose in interstitial fluid include (1) in-dwelling sensors, where a needle is utilized to insert the sensor into the dermis of the skin, and (2) ex-vivo sensors, where micro-needles penetrate the surface of the skin and the analyte is coupled from interstitial fluid to the sensor by diffusion to the sensor. In products, and in research, the biosensing of analytes in interstitial fluid monitoring has been dominated by metabolite analytes because electrochemical enzymatic sensors are readily available and well developed for these compounds, and because metabolites are found at generally high concentrations (mM) which simplifies their detection. Even so, use of an enzymatic sensor with a microneedle device has not yet seen commercial success, at least in part because microneedles have difficulty in keeping continuous contact with the dermis, and/or due to dermal compaction and changes in diffusion of glucose into the dermis. For an enzymatic sensor, which relies on a diffusive flux of analyte to the sensor, any change in coupling between the microneedles and the dermis of the skin would result in a false-change in measured glucose signal. Even in-dwelling sensors can suffer from motion artifacts as an enzymatic sensor's position in the dermis can impact diffusive flux of glucose to the sensor.

Affinity-based sensors such as electrochemical or optical aptamers are known to be inherently reversible (and thus truly continuous). They are also known to provide ranges of detections in the μM or lower ranges in biofluids such as whole blood. These sensors, however, are quite different than enzymatic sensors, which metabolize and therefore consume the analyte. This is because affinity sensors require equilibration of analyte concentration with the sensor itself, and have a known binding affinity for the target analyte. And so, affinity sensors could provide one or more advantages for metabolite sensing (glucose, lactate, ethanol, etc.). However, development of aptamers for metabolites has not been shown to be feasible. One issue that has hindered such development is the fact that the ability of aptamers to achieve high-affinity and selectivity to interact with target analyte depends strongly on functional groups or epitopes displayed by the target analyte. However, some classes of targets, such as monosaccharides, have scarce functionalities such that no aptamers have been reported to recognize, let alone distinguish from each other, glucose and other hexoses for example.

To deal with this, lab assays have demonstrated use of an adapter molecule which binds the metabolite (such as glucose), and then the combined metabolite and adapter are together able to bind to the aptamer. However, such an approach is ill-suited to a continuous wearable format, as the adapter molecules must be free in solution in order to be operative, but (at the same time) cannot be left free in solution where they could diffuse out of any device and into the body (because the adapter molecules are non-natural and thus present a potential for harm). As a result, using aptamers for continuous sensing of target analytes such as glucose remains an unresolved challenge.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sensing technology into proximity with biofluid and analytes.

Various aspects of the disclosed invention are directed to continuous aptamer base sensors for one or more analytes in interstitial fluid or other biofluids. The aspects of the present invention may more broadly adapt to other continuous sensors as well where an adapter molecule and aptamer are both required to detect the analyte.

One particular aspect of the present invention is directed to a device for detecting the presence of, or measuring the concentration or amount of, at least one analyte in a sample fluid. The device includes a sensor fluid, a plurality of adapter molecules in the sensor fluid that are capable of binding to an analyte, a plurality of aptamers in the sensor fluid that are capable of binding to the analyte when analyte is bound to one or more adapter molecules of the plurality of adapter molecules, at least one membrane in communication with the sensor fluid, and at least one detection component that is capable of detecting the binding of analyte by one or more of the plurality of aptamers. The membrane is permeable to the analyte but impermeable to the adapter molecule. The devices of the various embodiments may include those that are adapted to be outside of the body of the subject and outside the stratum-corneum of the skin of the subject. Alternatively, the device may be in-dwelling. And still alternatively, the device may be implanted.

Another aspect of the present invention is directed to a method for detecting the presence of, or measuring the concentration or amount of, at least one analyte in a sample fluid. The method includes bringing a sample fluid into contact with at least one adapter molecule of a plurality of adapter molecules that are present in a sensor fluid. This includes passing the sample fluid through a membrane that is permeable to analyte but impermeable to adapter molecules of the plurality of adapter molecules. Thereafter, the binding of analyte by one or more adapter molecules of the plurality of adapter molecules is detected or measured.

BRIEF DESCRIPTION OF THE DRAWINGS

The objects and advantages of the disclosed invention will be further appreciated in light of the following detailed descriptions and drawings in which.

DEFINITIONS

Figure 1A:
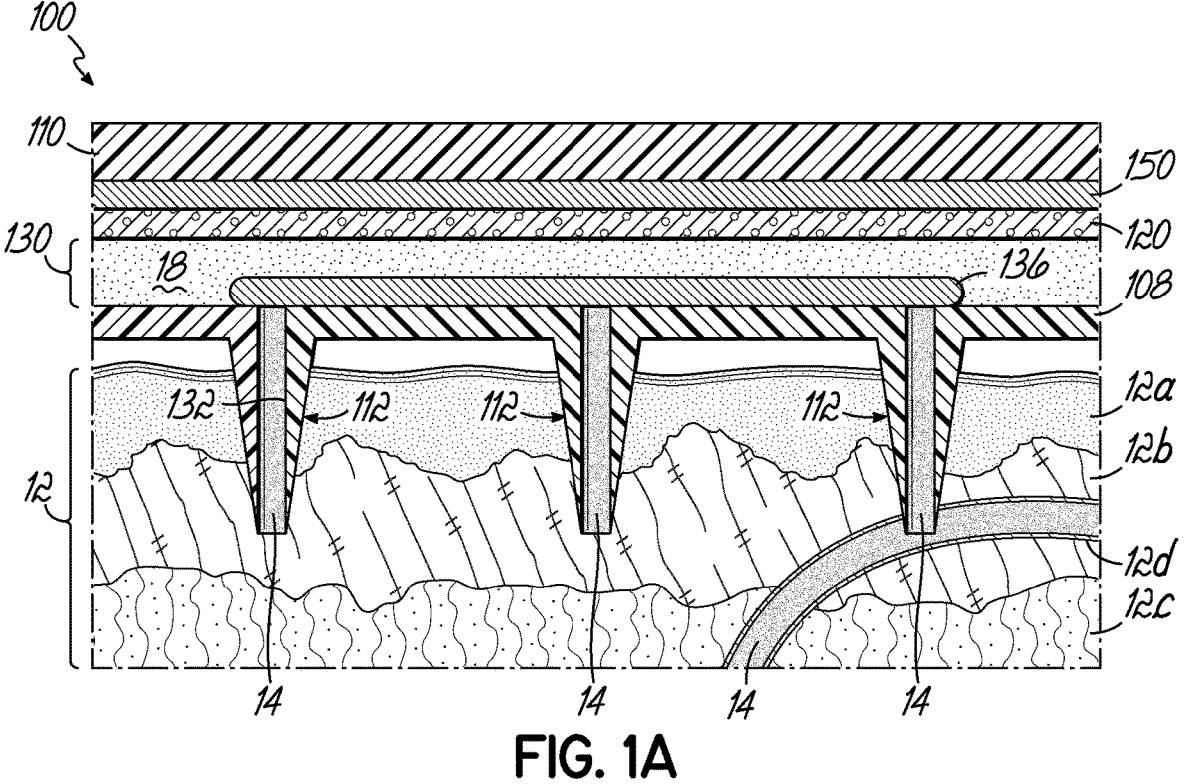
FIG. 1A is a cross-sectional view of a device in accordance with principles of the disclosed invention.

As used herein, "continuous sensing" with a "continuous sensor" means a sensor that changes in response to changing concentration of at least one solute in a solution such as an analyte. Similarly, as used herein, "continuous monitoring" means the capability of a device to provide multiple measurements of an analyte over time.

As used herein, the term "about," when referring to a value or to an amount of mass, weight, time, volume, pH, size, concentration or percentage is meant to encompass variations of ±20% in some embodiments, ±10% in some embodiments, ±5% in some embodiments, ±1% in some embodiments, ±0.5% in some embodiments, and ±0.1% in some embodiments from the specified amount, as such variations are appropriate to perform the disclosed method.

As used herein, the term "electrode" means any material that is electrically conductive such as gold, platinum, nickel, silicon, conductive liquid infused materials such as ionic liquids, PEDOT:PSS, conductive oxides, carbon, boron-doped diamond, nanotubes or nanowire meshes, or other suitable electrically conducting materials.

As used herein, the term "blocking layer" or "passivating layer" means a homogeneous or heterogeneous layer of molecules on an electrode which alter the electrochemical behavior of the electrode. Examples include a monolayer of mercaptohexanol on a gold electrode or as another example natural small-molecule solutes in serum that form a layer on a carbon electrode.

As used herein, the term "aptamer" means a molecule that undergoes a conformation or binding change as an analyte binds to the molecule, and which satisfies the general operating principles of the sensing method as described herein. Such molecules are, e.g., natural or modified DNA, RNA, or XNA oligonucleotide sequences, spiegelmers, peptide aptamers, and affimers. Modifications may include substituting unnatural nucleic acid bases for natural bases within the aptamer sequence, replacing natural sequences with unnatural sequences, or other suitable modifications that improve sensor function, but which behave analogous to traditional aptamers. Two or more aptamers bound together can also be referred to as an aptamer (i.e., not separated in solution). Aptamers can have molecular weights of at least 1 kDa, 10 kDa, or 100 kDa.

As used herein, the term "redox tag" or "redox molecule" means any species such as small or large molecules with a redox active portion that when brought adjacent to an electrode can reversibly transfer at least one electron with the electrode. Redox tag or molecule examples include methylene blue, ferrocene, quinones, or other suitable species that satisfy the definition of a redox tag or molecule. In some cases, a redox tag or molecule is referred to as a redox mediator. Redox tags or molecules may also exchange electrons or change in behavior when brought into proximity with other redox tags or molecules.

As used herein, the term "change in electron transfer" means a redox tag whose electron transfer with an electrode has changed in a measurable manner. This change in electron transfer can, for example, originate from availability for electron transfer, distance from an electrode, diffusion rate to or from an electrode, a shift or increase or decrease in electrochemical activity of the redox tag, or any other embodiment as taught herein that results in a measurable change in electron transfer between the redox tag and the electrode.

As used herein, the term "optical tag" or "fluorescent tag" means any species that fluoresces in response to an optical source such as LED and whose fluorescence is detectable by a photodetector such as a photodiode. Example fluorescent tags include fluorescein and may be used in combination with other fluorescent tags or optical quenchers such a black-hole quencher dyes to change the fluorescence of the optical tag.

As used herein, the term "signaling aptamer" means an aptamer that is tagged with a redox active molecule or tag and/or contains a redox active portion itself and which provides a change in electrochemical signal when it is released from an anchor aptamer.

As used herein, the term "anchor aptamer" means an aptamer that that can bind to a signaling aptamer, and when bound to the signaling aptamer changes at least one property of the bound vs. unbound signaling aptamer such as molecular weight, diffusion coefficient, charge state, being floating in solution vs. being immobilized, or some other property which causes a change in electron transfer with an electrode. The binding of the anchor aptamer with the signaling aptamer can be dependent on concentration of the analyte to be measured.

As used herein, the term "folded aptamer" means an aptamer that along its length associates with itself in one or more locations creating a three-dimensional structure for the aptamer that is distinct from an "unfolded aptamer" that is a freely floating and oscillating strand of aptamer. Aptamers can also be partially folded or partially unfolded in structure or in time spent in the folded vs. unfolded states. Multiple folding configurations are also possible.

As used herein, the term "analyte" means any solute in a solution or fluid which can be measured using a sensor. Analytes can be small molecules, proteins, peptides, electrolytes, acids, bases, antibodies, molecules with small molecules bound to them, DNA, RNA, drugs, chemicals, pollutants, or other solutes in a solution or fluid.

As used herein, the term "membrane" means a polymer film, plug of hydrogel, liquid-infused film, tiny pore, or other suitable material which is permiselective to transport of a solute through the membrane by solute parameters such as size, charge state, hydrophobicity, physical structure, or other solute parameters than can enable permiselectivity. For example, a dialysis membrane is permselective by passing small solutes but not large solutes such as proteins. Membranes as understood herein need not be multiporous, for example a nanotube or nanopore can act as a permiselective filter and is therefore considered part of a membrane as understood for the present invention. Permiselectivity can scale with the analyte, for example a membrane with a molecular weight cut-off of 50 kDa could be used to measure a 20-30 kDa protein but could still keep out cellular or other large content (globulins, fibrinogen, etc.) and retain in aptamer that adequately large or physically structured such that permeability through the membrane is slow or nil.

As used herein, the term "sample fluid" means any solution or fluid that contains at least one analyte to be measured.

As used herein, the term "sensor fluid" means a solution or fluid that differs from a sample solution by at least one property, and through which the sensor solution and the sample solution are therefore separated but are in fluidic connection through at least one pathway such as a membrane. The sensor solution comprises at least one aptamer as a solute.

As used herein, the term "reservoir fluid" means a solution or fluid that differs from a sample solution by at least one property, and through which the sensor solution and the reservoir solution are in fluidic connection through at least one pathway such as a membrane or a pin-hole connection. A reservoir fluid may have multiple function in a device, for example, by introducing a solute continuously or as needed by diffusion equilibrium into the sensor fluid, or for example removing unwanted solutes from a sensor fluid and acting as a "waste removal element".

As used herein, a "device" comprises at least one sensor based on at least one aptamer, at least one sensor solution, and at least one sample solution. Devices can sense multiple samples and be in multiple configurations such as a device to measure a pin-prick of blood, or a microneedle or in-dwelling sensor needle to measure interstitial fluid, or a device to measure saliva, tears, sweat, or urine sensor, or a device to measure water pollutants or food processing solutes, or other devices which measure at least one analyte found in a sample solution.

As used herein, "adapter" or "adapter molecule" means a molecule that when binding to a target analyte causes further binding of the target analyte and the adapter to an aptamer. The binding is reversible, and therefore enables a continuous sensor.

DETAILED DESCRIPTION OF THE INVENTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the disclosed invention are directed to continuous sensing of low-epitope analytes with aptamers.

Certain embodiments of the disclosed invention show sensors as simple individual elements. It is understood that many sensors require two or more electrodes, reference electrodes, or additional supporting technology or features which are not captured in the description herein. Sensors are preferably electrical in nature, but may also include optical such as a LED or laser excitation source and a photodetector, chemical, mechanical, or other known biosensing mechanisms. Sensors can be in duplicate, triplicate, or more, to provide improved data and readings. Sensors may provide continuous or discrete data and/or readings. Certain embodiments of the disclosed invention show sub-components of what would be sensing devices with more sub-components needed for use of the device in various applications, which are known (e.g., a battery, antenna, adhesive), and for purposes of brevity and focus on inventive aspects, such components may not be explicitly shown in the diagrams or described in the embodiments of the disclosed invention. All ranges of parameters disclosed herein include the endpoints of the ranges.

One particular aspect of the present invention is directed to a device for detecting the presence of, or measuring the concentration or amount of, at least one analyte in a sample fluid. The device includes a sensor fluid, a plurality of adapter molecules in the sensor fluid that are capable of binding to an analyte, a plurality of aptamers in the sensor fluid that are capable of binding to the analyte when analyte is bound to one or more adapter molecules of the plurality of adapter molecules, at least one membrane in communication with the sensor fluid, and at least one detection component that is capable of detecting the binding of analyte by one or more of the plurality of aptamers. The membrane is permeable to the analyte but impermeable to the adapter molecule. Another aspect of the present invention is directed to a method for detecting the presence of, or measuring the concentration or amount of, at least one analyte in a sample fluid. The method includes bringing a sample fluid into contact with at least one adapter molecule of a plurality of adapter molecules that are present in a sensor fluid. This includes passing the sample fluid through a membrane that is permeable to analyte but impermeable to adapter molecules of the plurality of adapter molecules. Thereafter, the binding of analyte by one or more adapter molecules of the plurality of adapter molecules is detected or measured.

Figure 1B:
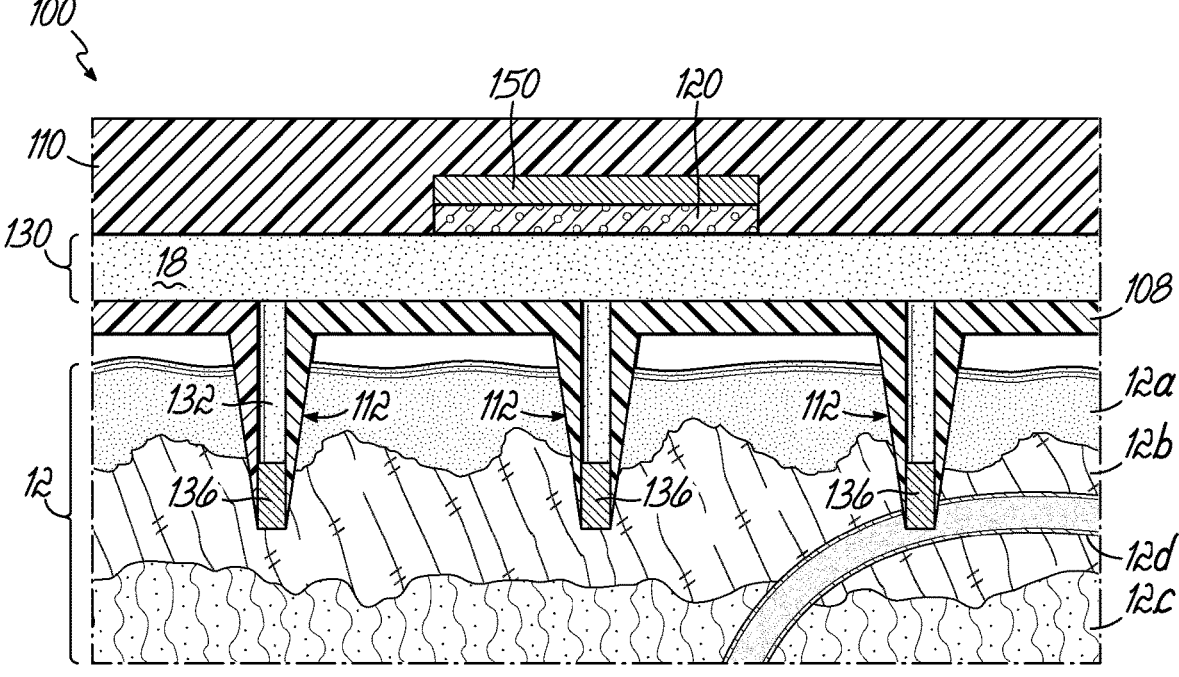
FIG. 1B is a cross-sectional view of an alternate embodiment of a device in accordance with principles of the disclosed invention.

With reference to FIGS. 1A and 1B, exemplary embodiments of devices in accordance with principles of the disclosed invention are shown. Referring first to FIG. 1A, a device 100 is shown as being placed partially in-vivo into the skin 12 of a subject. Skin 12 includes the epidermis 12a, the dermis 12b, and the subcutaneous or hypodermis 12c. The device 100 includes a feature 112 that allows for access to sample fluids from the subject. Such sample fluids may include interstitial fluid (from the dermis 12b) and/or blood (from a capillary 12d). In the embodiment shown in FIG. 1A, the feature 112 includes a plurality of microneedles (which may be formed of metal, polymer, semiconductor, glass, or other suitable material). Each of the microneedles 112 projects from a first substrate 108. And each microneedle 112 may include a hollow lumen 132. The device 100 also includes a second substrate 110 (which may be a material such as polymer or glass) having an electrode 150 adjacent thereto. An optional passivating layer 120 may be adjacent to electrode 150, such that electrode 150 is positioned between passivating layer 120 and second substrate 110. Passivating layer 120 includes a compound such as mercaptohexanol or may comprise natural solutes that have diffused into the device 100 from the dermis 12b.

As can be seen in FIG. 1A, a defined volume 130 is present between first substrate 108 and passivating layer 120. It will be recognized by those of ordinary skill in the art that defined volume 130 does not necessarily have to be defined by first substrate 108 and passivating layer 120— and in embodiments where passivating layer is absent, volume 130 may be defined by first substrate 108 and electrode 150; or, alternatively, may be defined by first substrate 108 and second substrate 110. A sensor fluid 18 may be present within volume 130 (as shown in FIG. 1A). Further, as can be seen in the embodiment of FIG. 1A, at least one membrane 136 is present between first substrate 108 and passivating layer 120, and is positioned adjacent first substrate 108. The at least one membrane 136 may be of various materials or substances—such as a dialysis membrane or hydrogel, for example. In the particular embodiment shown in FIG. 1A, portions of the membrane 136 overlie the boundary between volume 130 and lumens 132 of each microneedle 112. Due to this positioning of membrane 136, volume 130 includes sensor fluid 18, and lumens 132 include sample fluid 14—such as interstitial fluid from dermis 12b or blood from capillary 12d. Together the total volume provided by volume 130 and lumens 132 can be a microfluidic component such as channels, a hydrogel, or other suitable material. A diffusion or other fluidic pathway exists from the sample fluid 14, such as interstitial fluid or blood, into volumes 132, 130.

Another embodiment of a device 100 is shown in FIG. 1B. This embodiment also includes first and second substrates 108, 110, microneedles 112 having lumens 132, electrode 150, passivating layer 120, defined volume 130 and at least one membrane 136. As can be seen from FIG. 1B, in this embodiment, electrode 150 and passivating layer 120 are recessed in second substrate 110 (as opposed to the configuration shown in FIG. 1A). Thus, volume 130 is defined by first substrate 108 and combination of second substrate 110 and passivating layer 120. Further, the embodiment as shown in FIG. 1B includes a plurality of membranes 136, with each membrane 136 positioned in a distal end of each lumen 132 of each microneedle 112. Due to this positioning of membranes 136, both volume 130 and lumens 132 include a sensor fluid 18 (and sample fluid is present in, and obtainable from, dermis 12b and capillary 12d, for example).

Alternative arrangements and materials to those discussed above with respect to FIGS. 1A and 1B are possible, such as using a single needle or hydrogel polymer microneedles. In addition, one or more of the features of device 100 or the entire device 100 could be implanted into the body and perform similarly as described herein. Furthermore, a device 100 could be fully outside the body, if for example sampling a fluid such as sweat or tears.

Figure 2A:
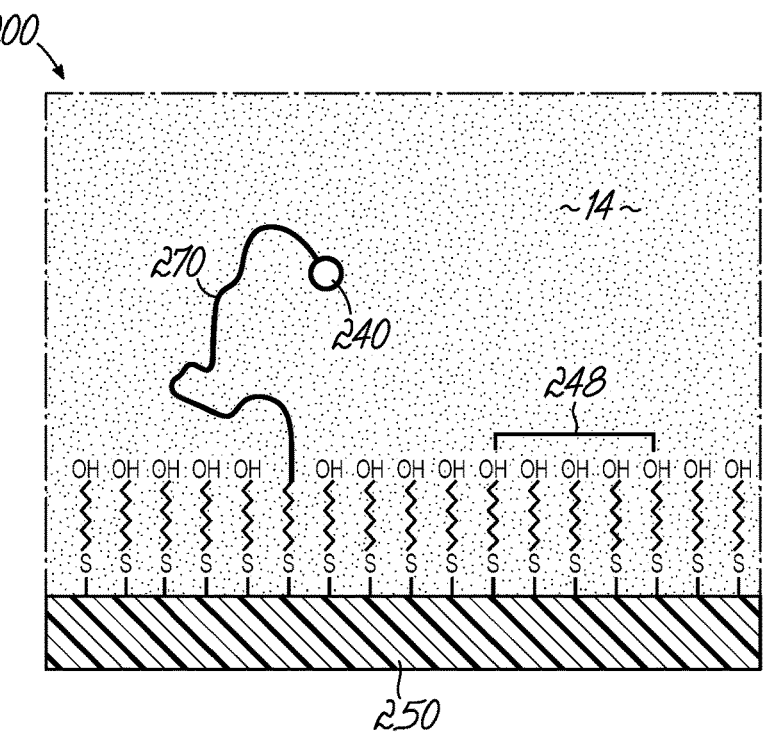
FIG. 2A is a schematic showing a prior art portion of an aptamer sensor device having a passivating layer and an aptamer attached to an electrode.
Figure 2B:
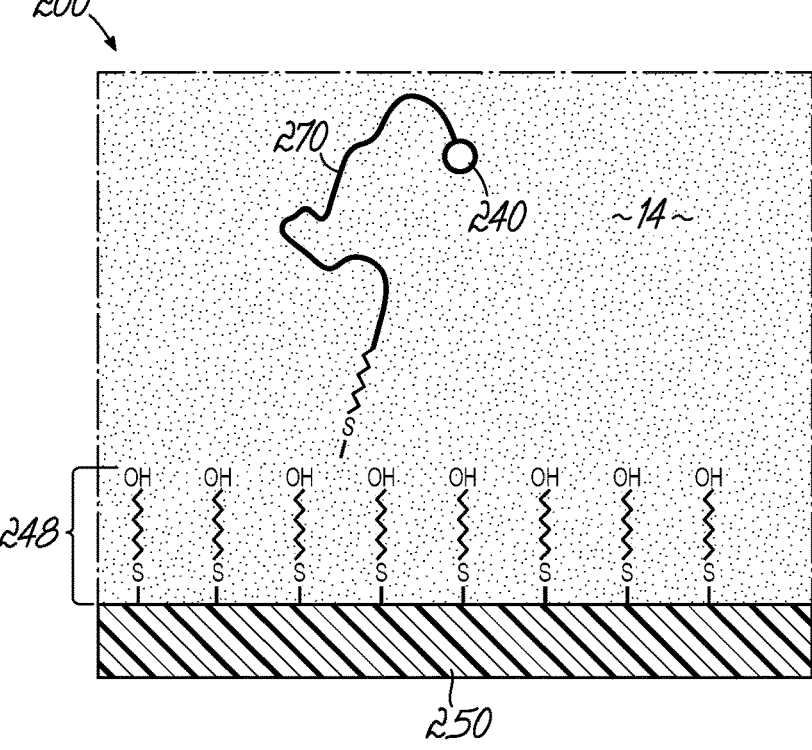
FIG. 2B is a schematic showing the aptamer and passivating layer portions of the aptamer sensor device of FIG. 2A degrading over time.

Turning now to FIGS. 2A and 2B, where like numerals refer to like features, a portion of a prior art device 200 is shown. Referring to FIG. 2A, an aptamer sensor includes a passivating or blocking layer 248 (including a compound such as mercaptohexanol) attached to an electrode 250 (made from a material such as gold), and having at least one aptamer 270 that is attached to the electrode 250, such as by being thiol-bonded to the electrode 250. The aptamer 270 has at least one redox tag or molecule 240, such as methylene blue, associated therewith. The device 200 is shown as being positioned in a sample fluid 14, such as blood or interstitial fluid (for example). This prior art device 200 may have an analyte (not shown) that binds with the aptamer 270, thereby changing the availability of the redox tag 240 to the electrode 250, such as by bringing it closer to, or further from, the electrode 250. Conventional aptamer sensors can be limited in performance because an aptamer that is bound to an electrode often has a weaker binding affinity to an analyte than an aptamer that is free in solution. In addition, as shown in FIG. 2B, the sensors can degrade as the aptamer 270 and/or blocking layer 248 degrades over time (e.g., chemical degradation, or detaching from the electrode 250). Also, because such prior art devices 200 have relied on exogenous molecules (e.g., mercaptohexanol) for passivation, the passivation layer 248 can also become thicker with fouling from solutes (such as albumin) in the sample fluid 14.

Figures 3, 4:
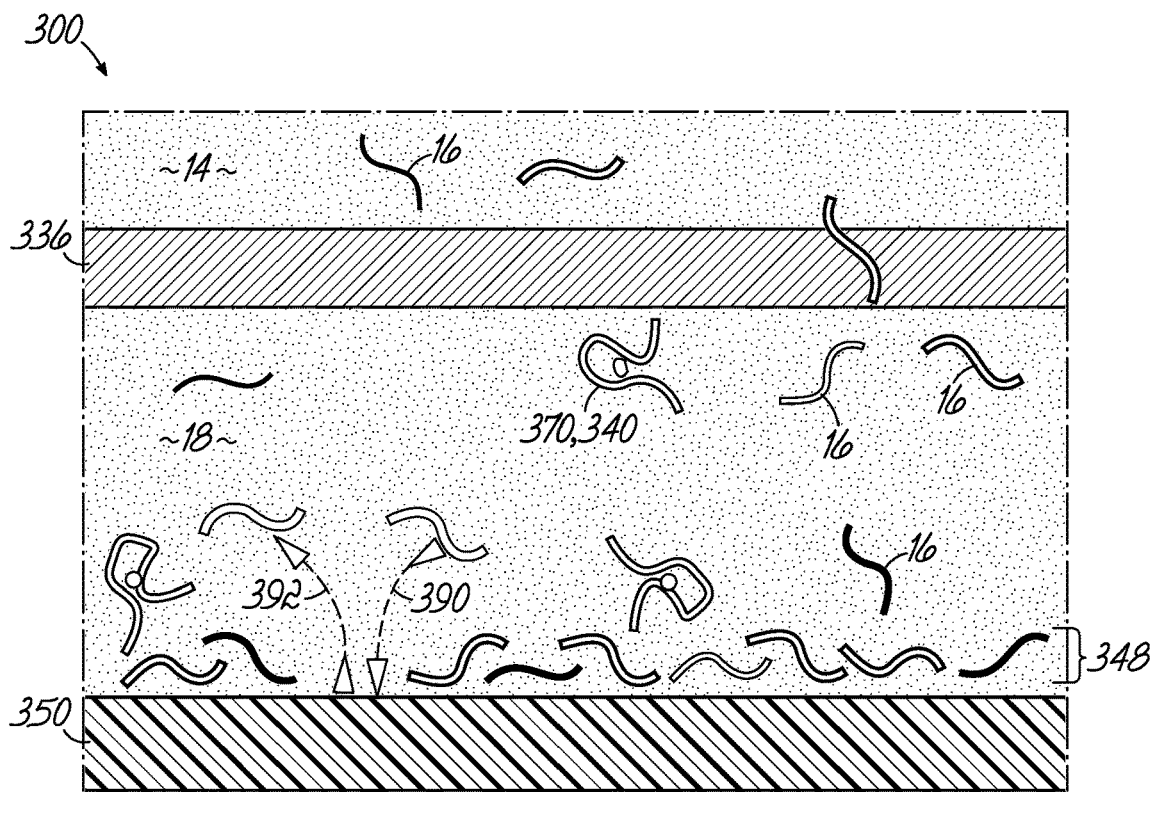
FIG. 3 is a schematic of yet another embodiment of a device in accordance with principles of the present invention.
FIG. 4 is a graph showing the effect of a membrane in an aptamer sensor device on percentage of solute retention versus molecular weight of the solute.

Thus, and with reference now to FIG. 3, where like numerals refer to like features, an embodiment of the disclosed invention that improves on the prior art devices and reduces or eliminates drawbacks with such devices is shown. To that end, FIG. 3 shows a device 300 (or at least a portion thereof) that includes an electrode 350 and at least one membrane 336 which separates a sample fluid 14 from a sensor fluid 18. The sensor fluid 18 contains a plurality of aptamers 370 having redox tags 340. The electrode 350 may include a passivating layer 348. The passivating layer 348 may comprise one or more endogeneous solutes 16 from the sample fluid 14 itself (or, as initially prepared, the passivating layer 348 may be prepared from molecules that are known to be endogenous to the sample fluid to be tested). Examples of such endogenous molecules 16 include small molecules such as amino acids, hormones, metabolites, or peptides. (Thus, the device 300 shown in FIG. 3 differs from that described above in prior art FIGS. 2A and 2B in that the prior art device described above included an aptamer and an exogenous molecule, such as mercaptohexanol. Similarly, electrode 350 could also contain a passivation layer 348 comprised, at least in part, by an exogenous molecule such as hexanethiol or mercaptohexanol. But, even in that case, the passivation layer could detatch from the electrode 350 and be in need of replacement.) By including endogeneous molecules 16 in the passivation layer 348, longer lifetime of the device 300 is achieved because endogenous molecules 16 can leave the electrode 350 as shown by arrow 392 and another endogenous molecule 16 can replace that now-missing molecule as shown by arrow 390. Thus, in a sense, the very molecules in the sample fluid 14 can be used to "repair" the passivation layer as it degrades, thereby extending the life of the device. (As mentioned above, these endogenous molecules can originate from the sample fluid itself, be already present as a deliberate component of the sensor fluid, or could be a mix of the two.) As a non-limiting example, membrane 336 is able to pass in small solutes (e.g., <1 kDa)—for example, an analyte such as cortisol—and passivating solutes 16, such as amino-acids and peptides, but retains the aptamer 370 (with redox tag 340) which is often >10 kDa in molecular weight. If the aptamer 370 with redox tag 340 were not retained by the membrane 336, then aptamer 370 with redox tag 340 could be lost into the body and no longer able be able to provide a measurement of the analyte.

An example of the analysis of the use of a membrane to pass small solutes (small target analyte) while retaining aptamers within device is shown with reference to FIG. 4, which shows an illustrative plot of solute retention for a membrane such as membrane 336. This is an example only, and shows that if measuring a small analyte such as cortisol (<400 Da) and using a large aptamer (>10 kDa or even >50 kDa) a membrane could be highly permeable to the analyte and poorly permeable to the aptamer. Thus, for example, in various embodiments, membranes of the present invention may have molecular weight cutoffs (i.e., the molecular weight above which a molecule will not easily pass through the membrane) that are at least one of <300 Da, <1000 Da, <3 kDa, <10 kDa, <30 kDa, <100 kDa, <300 kDa. Larger molecular weight cut-off membranes will require larger sized aptamers to prevent the aptamers from potentially escaping the device.

Several additional embodiments will be discussed below. In these additional embodiments, an increase in availability of the redox tag to the electrode can occur as a result of aptamer binding analyte, or, alternatively, without aptamer binding to an analyte. And even though each of the embodiments discussed below (and their respective figures) may show one specific example, the other the embodiments of the invention are not so limited (e.g., the various aptamer/redox tag types can be used across the various embodiments of devices disclosed herein, and vice versa.

Figure 5A:
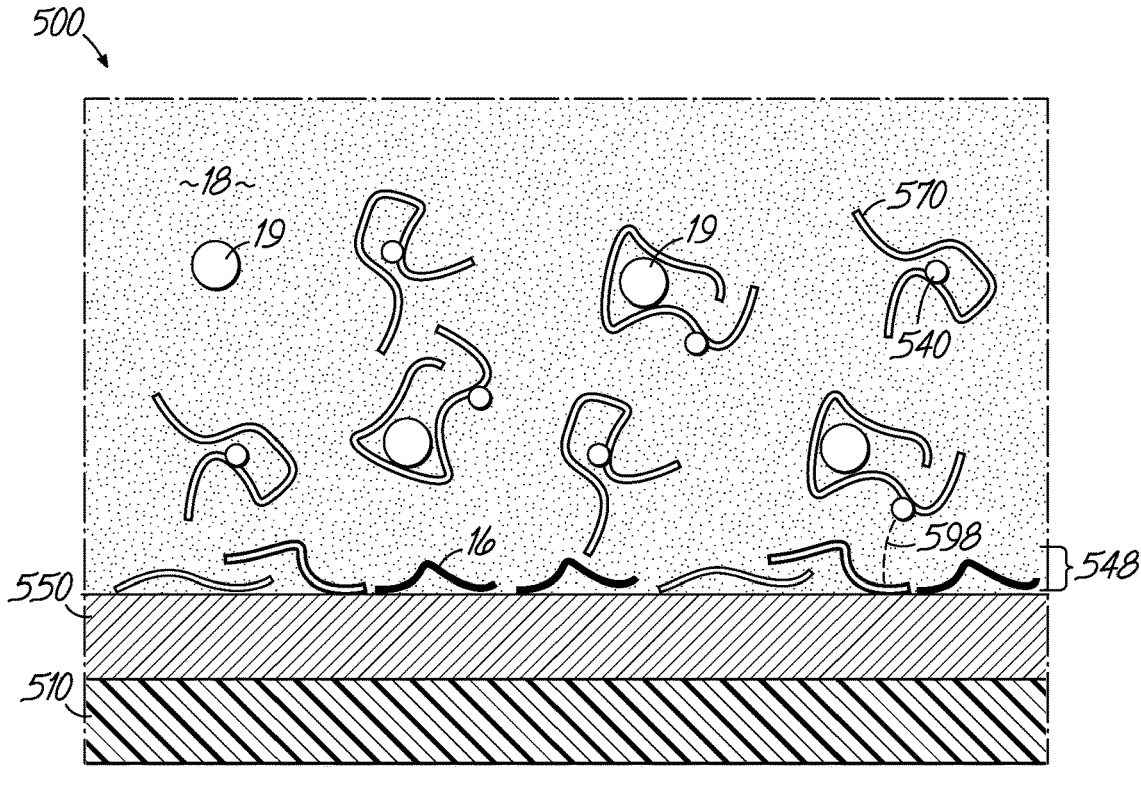
FIG. 5A is a schematic of yet another embodiment of a device in accordance with principles of the present invention.

Turning now to FIGS. 5A-5E, where like numerals refer to like features: FIG. 5A shows a portion of a device 500 including a substrate 510, a sensor fluid 18, a plurality of aptamers 570 with redox tags 540 free in the sensor fluid 18, a passivation layer 548 of endogenous solutes 16, and an electrode adjacent the substrate 510. Though not part of the device, analytes 19 are also depicted as present in the sensor fluid of the device. The schematic shown in FIG. 5A also depicts an electron transfer event that occurs between a redox tag 540 and the electrode 550. This is shown generally at reference numeral 598, and is a non-limiting example depicting that electron transfer 598 from a redox tag 540 occurs in an increased amount, or frequency, or rate, when aptamer 570 binding to analyte 19 occurs (e.g., as shown in the figure, when analyte is not bound to aptamer, the redox tag is not available—or is less available—to the electrode, due to, for example, a conformation of the aptamer that hinders or prevents such transfer when not bound to analyte; conversely, when aptamer binds analyte, the conformation of aptamer may change in a manner that positions the redox tag for electron transfer). In various embodiments, aptamer binding to analyte can provide changes in electron transfer and redox current (compared to baseline transfer and current—i.e., transfer/current in the absence of analyte binding) of greater than 5%, greater than 10%, greater than 20%, greater than 50%, greater than 100%, or greater than 200%. For the embodiments illustrated herein, non-limiting examples of electrical measurement techniques may include voltammetry, square wave voltammetry, amperometry, chronoamperometry, coulometry, chronocoulometry, with a preferred embodiment being square wave voltammetry.

Figure 5B:
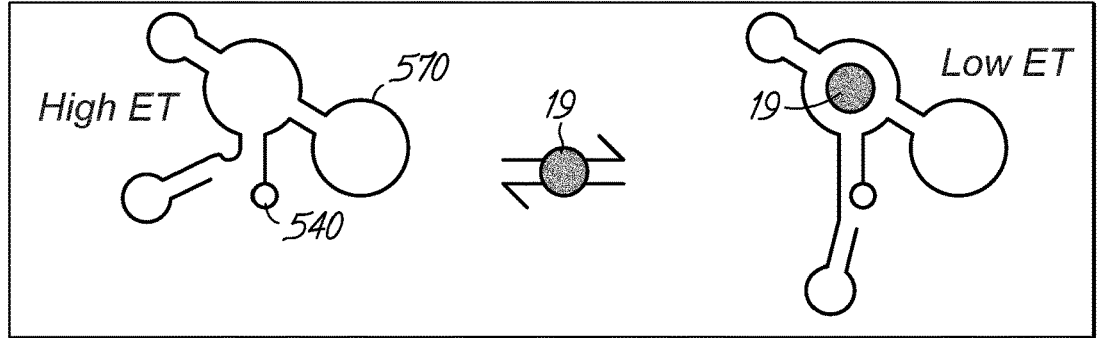
FIG. 5B is a schematic showing an alternate embodiment of an aptamer with attached redox tag that can be used with devices in accordance with principles of the disclosed invention.

FIG. 5B schematically depicts another example of an aptamer 570 with attached redox tag 540 (that differs from the aptamer 570/redox tag 540 schematically shown in FIG. 5A). The embodiment of the aptamer 570 in FIG. 5B is designed such that the redox tag 540 is more available for electron transfer with the electrode 550 in the absence of any analyte 19 binding to the aptamer 570 (high electron transfer—or high ET). Conversely, when analyte 19 binds to the aptamer 570 of FIG. 5B, the redox tag 540 is less available for electron transfer with the electrode 550 (e.g., the redox tag 540 is less exposed—low ET).

Figure 5C:
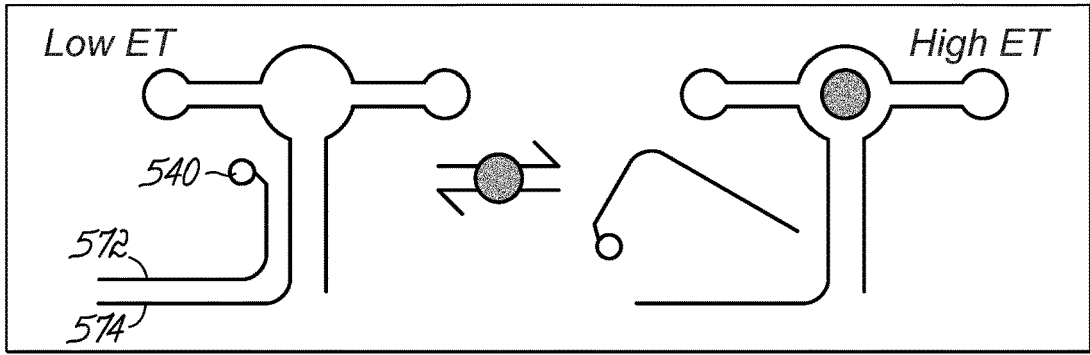
FIG. 5C is a schematic showing yet another alternate embodiment of an aptamer with attached redox tag that can be used with devices in accordance with principles of the disclosed invention.

FIG. 5C schematically depicts yet another example of an aptamer with attached redox tag 540 (that differs from the aptamer 570/redox tag 540 schematically shown in FIGS. 5A and 5B). The embodiment shown in FIG. 5C is designed with two aptamer portions: a signaling aptamer 572 and an anchor aptamer 574. A redox tag 540 is associated with (such as by being attached to) the signaling aptamer 572. The anchor aptamer 574 includes a portion that has affinity for, and thus can bind, analyte 19. When analyte 19 is not bound to the anchor aptamer 574 (left side of FIG. 5C), the signaling aptamer 572 remains associated with the anchor aptamer 574, and so the redox tag 540 on signaling aptamer 572 is less available for electron transfer with the electrode 550 (low ET). However, once the anchor aptamer 574 binds to analyte 19 (right side of FIG. 5C), signaling aptamer 572 is released from anchor aptamer 574, and the redox tag 540 becomes more available for electron transfer with the electrode 550 (high ET). It will be recognized that the device of the embodiment of FIG. 5C has a plurality of aptamers—and thus includes a plurality of signaling aptamers 572, and a plurality of anchor aptamers 574. As described above, each anchor aptamer of the plurality of anchor aptamers is adapted to bind to analyte. In one embodiment, each signaling aptamer of a majority of the plurality of signaling aptamers is bound to a respective anchor aptamer when a majority of anchor aptamers are not bound to any analyte. (This may occur, for example, prior to the introduction of any analyte.) Once analyte is introduced (such as when a sample fluid is introduced into the device—e.g., by being introduced into the sensor fluid of the device), at least a subset of anchor aptamers from the plurality of anchor aptamers then binds to analyte. When this occurs, a subset of signaling aptamers (from the total plurality of aptamers) dissociates from the anchor aptamers—and the redox tag becomes more available for electron transfer with the electrode.

Further, while the embodiment shown in FIG. 5C depicts analyte 19 binding to anchor aptamer 574 and redox tag 540 on signaling aptamer 572, in an alternate embodiment analyte binding may occur with signaling aptamer (signaling aptamer having redox tag), and binding of analyte to signaling aptamer may serve to release signaling aptamer from anchor aptamer (such as by change in conformation of signaling aptamer). Even further configurations as possible, as understood by those skilled in the art of aptamers. To maximize the signal gain (change in signal) signaling aptamer 572 concentration will typically be less than or equal to the anchor aptamer 574 concentration else the signaling aptamer can cause increased background signal with or without the presence of analyte.

Figure 5D:
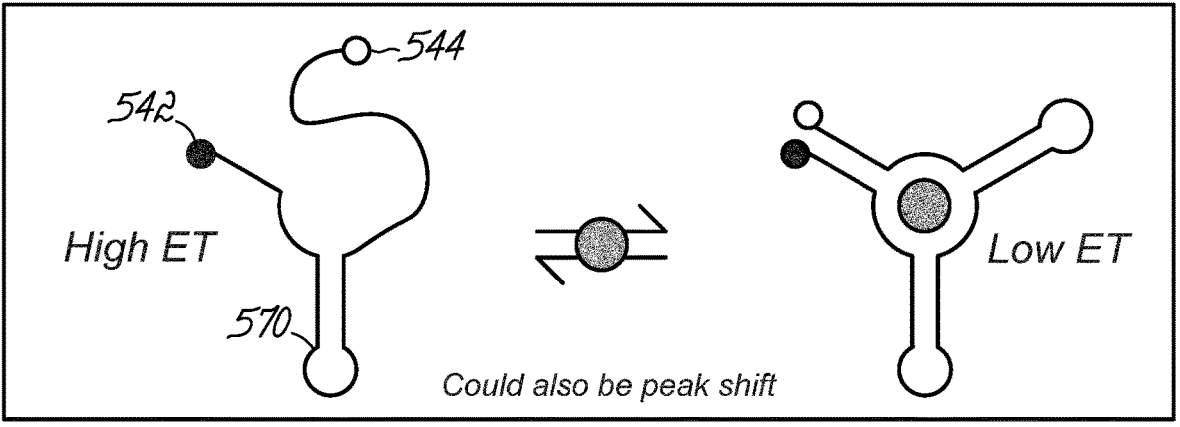
FIG. 5D is a schematic showing yet another alternate embodiment of an aptamer with attached redox tag that can be used with devices in accordance with principles of the disclosed invention.

FIG. 5D schematically depicts yet another example of an aptamer with attached redox tag 540 (that differs from the aptamers/redox tags schematically shown in FIGS. SA, 5B, and SC). The embodiment of the aptamer 570 in FIG. 5D has both a redox tag 544 and a redox quencher 542 associated therewith (such as by being bound to the aptamer 570). When analyte 19 is not bound to the aptamer 570, the redox tag 544 and redox quencher 542 are spatially separated (left side of FIG. 5D) thereby allowing for greater electron transfer between redox tag 544 and electrode 550 (high ET). However, once the aptamer 570 binds to analyte 19 (right side of FIG. 5D), the redox tag 544 and redox quencher 542 are brought into closer proximity with one another, thereby causing less electron transfer between redox tag 544 and electrode 550 (low ET). Numerous quenchers are possible, including anthraquinone-based redox molecules that can self-quenching when two of such identical molecules are brought close together (monomer vs. dimer).

Figure 5E:
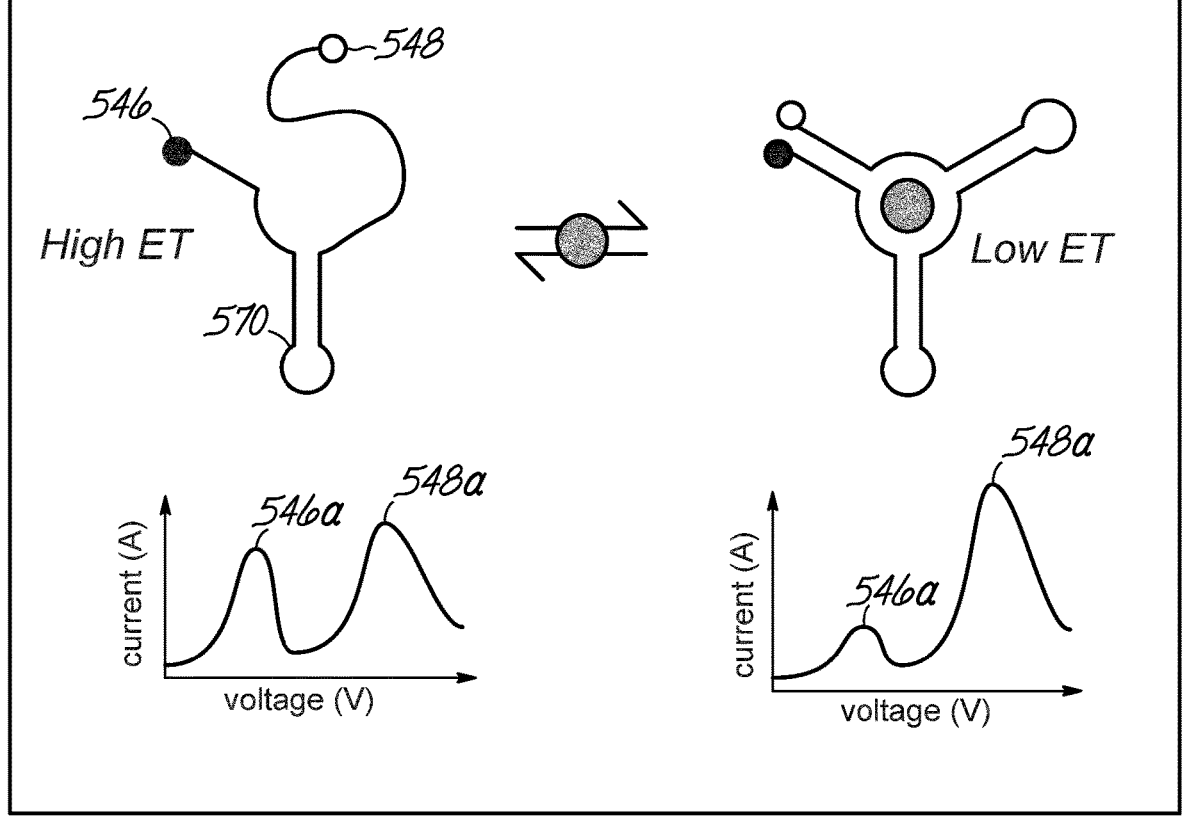
FIG. 5E is a schematic showing yet another alternate embodiment of an aptamer with attached redox tag that can be used with devices in accordance with principles of the disclosed invention.

FIG. 5E schematically depicts yet another example of an aptamer with attached redox tag 540 (that differs from the aptamers/redox tags schematically shown in FIGS. SA, 5B, SC, and SD). The embodiment of the aptamer 570 in FIG. 5E has both a first redox tag 546 and a second redox tag 548 associated therewith (such as by being bound to the aptamer 570). When analyte 19 is not bound to the aptamer 570, the first and second redox tags 546, 548 are spatially separated (left side of FIG. 5E) thereby allowing for greater electron transfer between first and second redox tags 546, 548 and electrode 550 (high ET). However, once the aptamer 570 binds to analyte 19 (right side of FIG. 5E), the first and second redox tags 546, 548 are brought closer together and the electron transfer from one of the redox tags 546, 548 to the electrode 550 is altered due to a two-step mediated electron transfer process, or other effect, for two redox tags brought into close proximity. These changes in electron transfer are depicted in the voltammograms as shown as 546a and 548a. A non-limiting example of redox tags that enable the embodiment of FIG. 5E include methylene blue and ferricyanide.

Figure 6A:
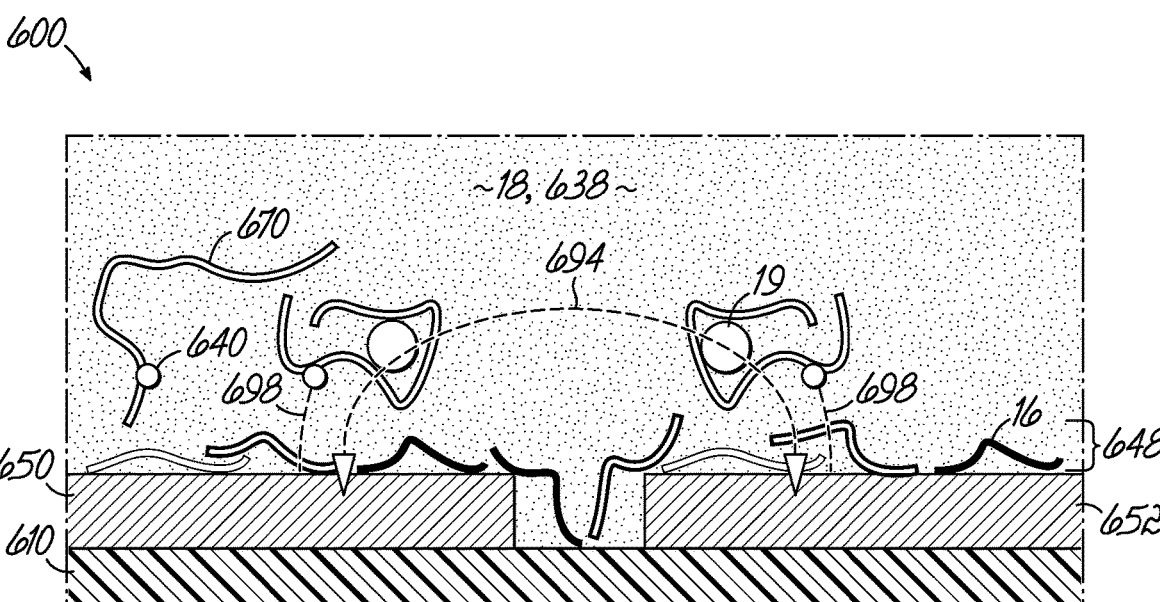
FIG. 6A is a schematic of yet another embodiment of a device in accordance with principles of the present invention.
Figure 6B:
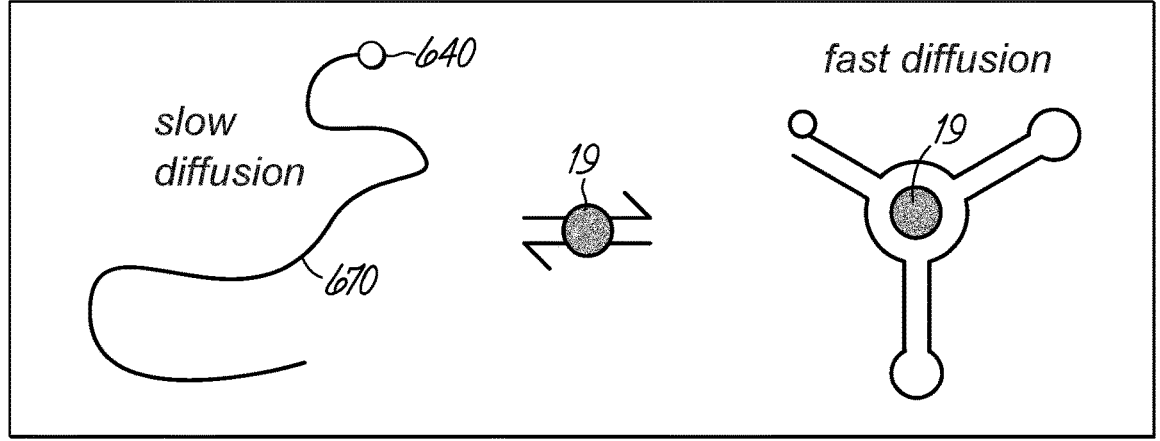
FIG. 6B is a schematic showing an alternate embodiment of an aptamer with attached redox tag that can be used with devices in accordance with principles of the disclosed invention.
Figure 6C:
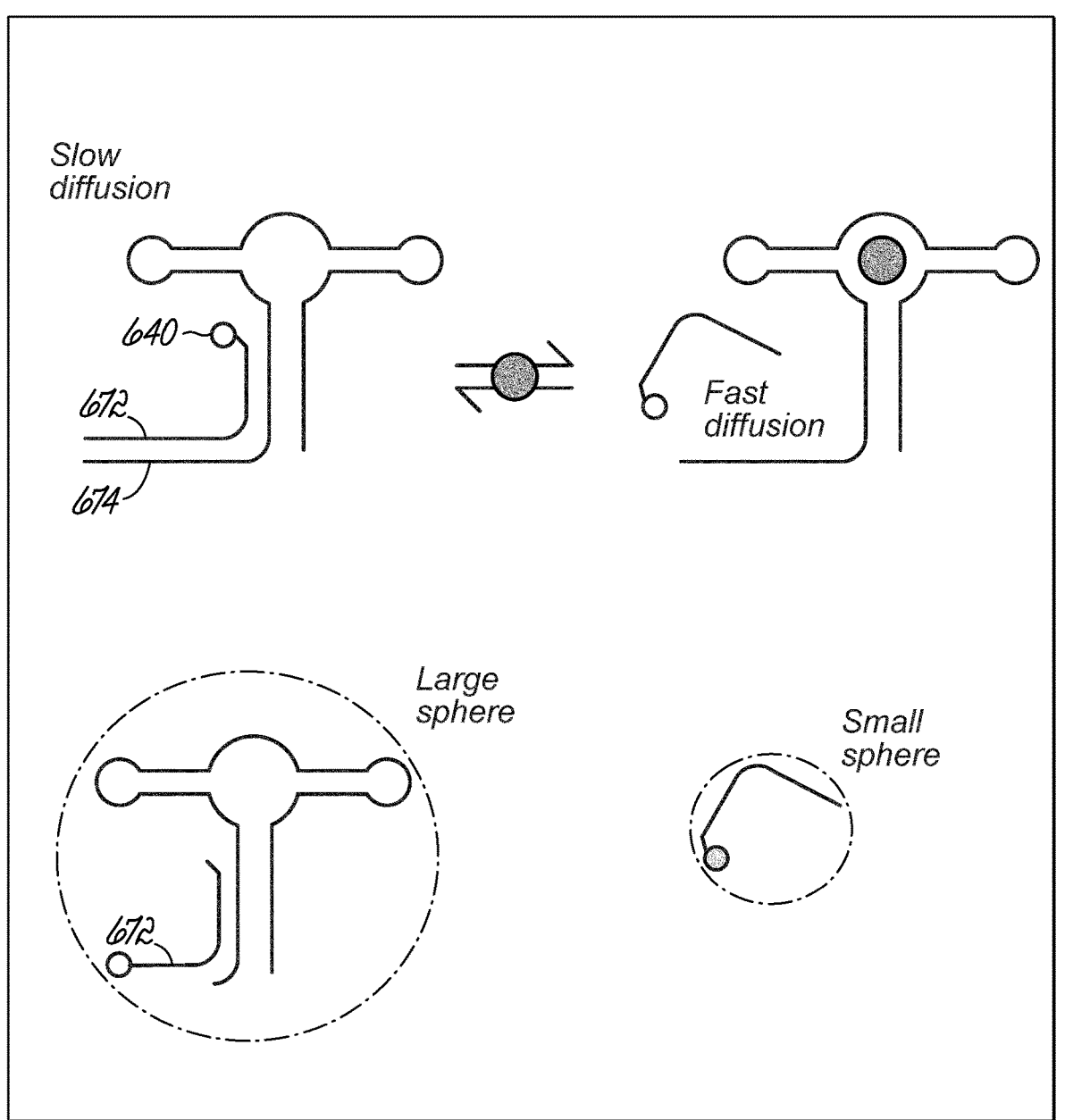
FIG. 6C is a schematic showing yet another alternate embodiment of an aptamer with attached redox tag that can be used with devices in accordance with principles of the disclosed invention.

Turning now to FIGS. 6A-6C, where like numerals refer to like features: FIG. 6A shows a portion of a device 600 that includes a substrate 610, at least first and second electrodes 650, 652, a passivation layer 648 including endogenous solutes 16, a sensor fluid 18 (which, in the embodiment illustrated in FIG. 6A is inside an optional hydrogel 638), a plurality of aptamers 670 having redox tags 640 (free in solution), and a diffusion or iontophoretic pathway 694. Though not part of the device, analytes 19 are also depicted as present in the sensor fluid of the device. FIG. 6A also schematically depicts electron transfer that can occur between redox tags 640 and the first and second electrodes 650, 652. As can be seen in FIG. 6A, as a non-limiting example, electron transfer 698 from the redox tags 640 in an increased amount, or frequency, or rate, when analyte 19 is bound to the aptamer 670. For example, when analyte is bound to aptamer, the hydrodynamic radius or size of the aptamer is smaller and therefore providing a faster diffusion coefficient, which results in the redox tag being more available for electron transfer with the electrodes (such a version will be discussed in greater detail below with respect to FIG. 6B); or, for example, when analyte is not bound to aptamer, the redox tag is not available—or is less available—to the electrode, due to, for example, a conformation of the aptamer that hinders or prevents such transfer when not bound to analyte; conversely, when aptamer binds analyte, the conformation of aptamer may change in a manner that positions the redox tag for electron transfer. In various embodiments, aptamer binding to analyte can provide changes in electron transfer and redox current (compared to baseline transfer and current—i.e., transfer/current in the absence of analyte binding) of greater than 5%, greater than 10%, greater than 20%, greater than 50%, greater than 100%, or greater than 200%. For the embodiments illustrated in FIGS. 6A-6C, non-limiting examples of electrical measurement techniques may include voltammetry, square wave voltammetry, amperometry, chronoamperometry, coulometry, chronocoulometry, with a preferred embodiment being amperometry.

FIG. 6B schematically depicts another example of an aptamer 670 with attached redox tag 640 (that differs from the aptamer 670/redox tag 640 schematically shown in FIG. 6A). The embodiment of the aptamer in FIG. 6B is designed such that the redox tag 640 is less available for electron transfer with the electrodes 650, 652 in the absence of analyte binding to aptamer (left side of FIG. 6B), because of a longer diffusion time between the first and second electrodes 650, 652 where the analyte can undergo redox recycling (e.g. one electrode is a reducing electrode, one electrode is an oxidizing electrode). However, when analyte 19 binds to the aptamer 670 (right side of FIG. 6B), the hydrodynamic radius or size of the aptamer is smaller and therefore providing a faster diffusion coefficient, and therefore redox tag 640 is more available for electron transfer with the first and second electrodes 650, 652. The binding of analyte 19 transforms the aptamer 670 between a long unfolded aptamer 670 (in the absence of analyte 19 binding) and an aptamer 670 with three stems when analyte 19 binds to aptamer 670.

As described above, with respect to FIG. 6A, a non-limiting example of an environment within a device 600 may include an optional hydrogel. In such an embodiment, the hydrogel 638 (such as agar or polyacrylamide) is added to further distinguish diffusion times between aptamers 670 bound to analyte 19 and aptamers 670 not bound to analyte. This is because the hydrogel 638 creates a more tortuous and size-selective diffusion pathway than a pure fluid would by itself. For example, an aptamer 670 that fully dissociates could be modified to have a significant change in hydrodynamic radius (R), which changes its diffusion coefficient (D) according to D=kT/(6πηR). This equation is for diffusion in pure solution; a dense hydrogel 638 can be added to further distinguish the diffusion of the unfolded aptamer vs. the folded aptamer. The resulting current between the redox recycling electrodes is proportional as I∝D C/z, where C is the concentration of the aptamer 670 and z the electrode-to-electrode distance. With respect to changes in signal gain, the diffusion length of oglionucleotides (aptamers) varies with length to the ~0.6th power, and a 15 kDa protein that is globular/unfolded can have a change in R of 2.15/3.65.

FIG. 6C schematically depicts yet another example of an aptamer 670 with attached redox tag 640 (that differs from the aptamer 670/redox tag 640 schematically shown in FIGS. 6A and 6B). The embodiment of the aptamer in FIG. 6C is designed with two aptamer portions: a signaling aptamer 672 and an anchor aptamer 674. A redox tag 640 is associated with (such as by being attached to) the signaling aptamer 672. The anchor aptamer 674 includes a portion that has affinity for, and thus can bind, analyte 19. When analyte 19 is not bound to the anchor aptamer 674 (left side of FIG. 6C), the signaling aptamer 672 remains associated with the anchor aptamer 674, and so the redox tag 640 on signaling aptamer 672 is less available for electron transfer with the first and second electrode 650, 652 (as the combined signaling and anchor aptamers 672, 674 will exhibit slower diffusion in sensor solution and hydrogel). However, once the anchor aptamer 674 binds to analyte 19 (right side of FIG. 6C), signaling aptamer 672 is released from anchor aptamer 674, and the redox tag 640 becomes more available for electron transfer with the first and second electrodes 650, 652 (as the liberated signaling aptamer 672 will exhibit more rapid diffusion in sensor solution and hydrogel). Further, while the embodiment shown in FIG. 6C depicts analyte 19 binding to anchor aptamer 674 and redox tag 640 on signaling aptamer 672, in an alternate embodiment analyte binding may occur with signaling aptamer (signaling aptamer having redox tag), and binding of analyte to signaling aptamer may serve to release signaling aptamer from anchor aptamer (such as by change in conformation of signaling aptamer).

It will be recognized that when the device shown in FIG. 6A uses the embodiment of aptamers of FIG. 6C, it will include a plurality of signaling aptamers 672, and a plurality of anchor aptamers 674. As described above, each anchor aptamer of the plurality of anchor aptamers is adapted to bind to analyte. In one embodiment, each signaling aptamer of a majority of the plurality of signaling aptamers is bound to a respective anchor aptamer when a majority of anchor aptamers are not bound to any analyte. (This may occur, for example, prior to the introduction of any analyte.) Once analyte is introduced (such as when a sample fluid is introduced into the device—e.g., by being introduced into the sensor fluid of the device), at least a subset of anchor aptamers from the plurality of anchor aptamers then binds to analyte. When this occurs, a subset of signaling aptamers (from the total plurality of aptamers) dissociates from the anchor aptamers—and the redox tag becomes more available for electron transfer with the electrode.

With further reference to FIG. 6C, in addition to changes in diffusion coefficient, the larger the effective sphere for the aptamer the less likely it will experience electron transfer with an electrode (with a first principles estimation based on the inverse of sphere area, proportional to 1/R^2). This example is simply to show that two factors can be at play for embodiments of the present invention, both distance of the redox tag to the electrode and diffusion time to/from the electrode. This diffusion time to an electrode applies other embodiments as well, where for example with a chrono-amperometric response for an aptamer the total current baseline could remain higher or reach baseline more quickly as diffusion coefficient for the aptamers increases. This diffusion time to an electrode may also impact interrogation methods such as square wave voltammetry, as aptamer that is near the electrode can contribute to the signal as well if it is able to diffuse to the electrode during each square window (during each voltage pulse that is applied). The first and second electrodes 650 and 652 can be closely spaced via interdigitation or other suitable technique, and, in such an embodiment, may be within less than 50 μm, less than 10 μm, less than 2 μm, or less than 0.4 μm distant of each other.

Figure 7:
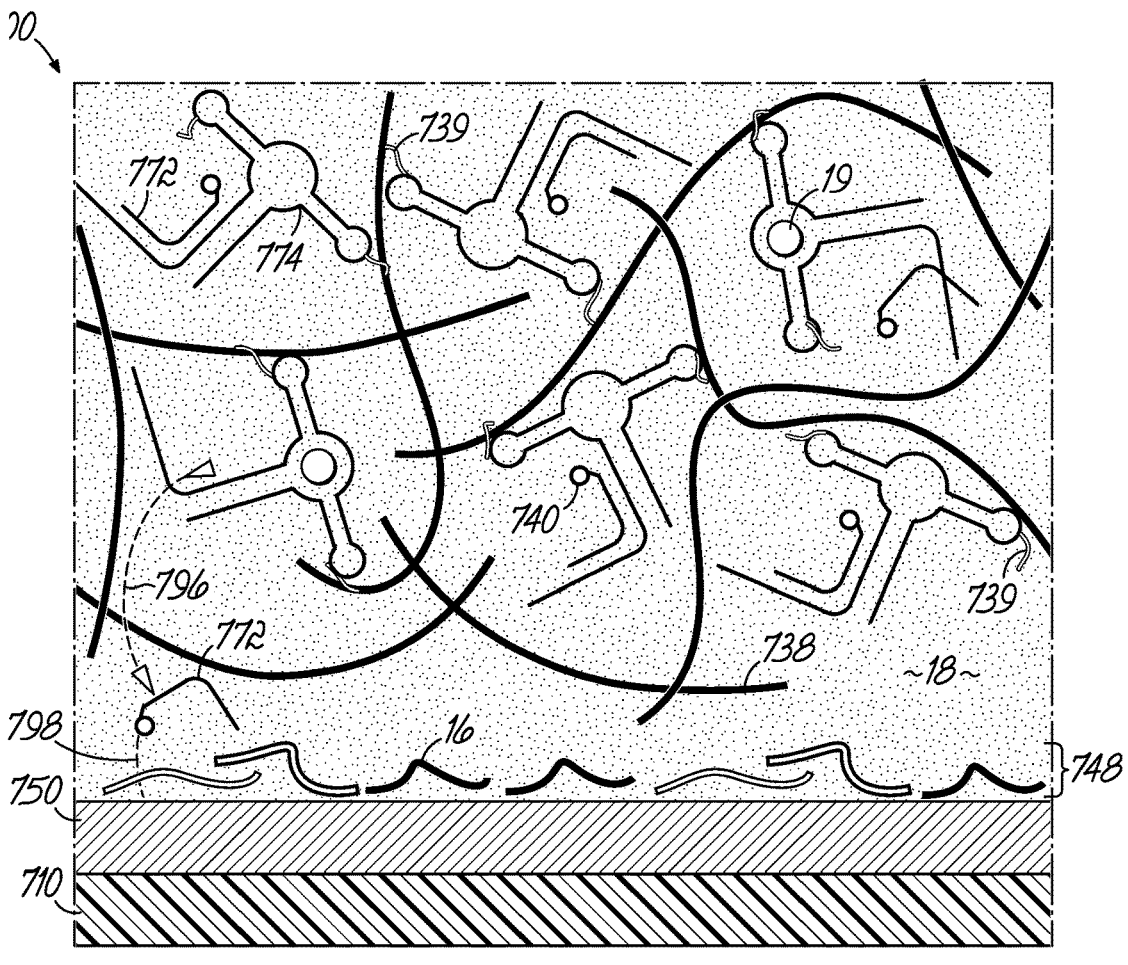
FIG. 7 is a schematic of yet another embodiment of a device in accordance with principles of the present invention.

With reference to FIG. 7 where like numerals refer to like features, another embodiment in accordance with aspects of the present invention is shown. As can be seen in FIG. 7, a portion of a device 700 is shown, and includes a substrate 710, at least one electrode 750, a passivation layer 748 including endogenous solutes 16, a sensor fluid 18, a plurality of aptamers having redox tags 740 (free in the sensor solution), and a poorly-mobile or non-mobile material 738 in the sensor fluid 18. Though not part of the device, analytes 19 are also depicted as present in the sensor fluid of the device.

The aptamers/redox tags component of the embodiment of FIG. 7 is similar to that shown in FIGS. 5C and 6C, and includes two aptamer portions: a signaling aptamer 772 and an anchor aptamer 774. A redox tag 740 is associated with (such as by being attached to) the signaling aptamer 772. The anchor aptamer 774 includes a portion that has affinity for, and thus can bind, analyte 19. As can be seen in FIG. 7, the anchor aptamer 774 is immobilized via linkage 739 to the poorly or non-mobile material 738. The poorly-mobile or non-mobile material 738 may comprise various materials, such as a hydrogel. In one non-limiting example, the material 738 could be a hydrogel such as polyacrylamide and the linker be a molecule such as acrydite that is attached to the anchor aptamer at a terminal end or other location. In an alternate embodiment, the anchor aptamer could be cross-linked with other anchor aptamers or the anchor aptamer made so large (e.g., >100 kDa) such that it is effectively immobile in a dense hydrogel 738.

Still referring to FIG. 7, when analyte 19 is not bound to the anchor aptamer 774, the signaling aptamer 772 remains associated with the anchor aptamer 774, and so the redox tag 740 on signaling aptamer 772 is less available for electron transfer with the electrode 750 (because the combined signaling and anchor aptamers 772, 774 will be poorly-mobile or non-mobile in the sensor fluid due to anchor aptamer 774 being linked to material 738). However, once the anchor aptamer 774 binds to analyte 19, the signaling aptamer 772 is released from anchor aptamer 774 (as indicated by arrow 796), and the redox tag 740 becomes more available for electron transfer with the electrode 750 (because the liberated signaling aptamer 772 will exhibit more rapid diffusion in sensor solution as it is no longer complexed with the anchor aptamer 774 that is linked to poorly-mobile or non-mobile material 738). Further, while the embodiment shown in FIG. 7 depicts analyte 19 binding to anchor aptamer 774 and redox tag 740 on signaling aptamer 772, in an alternate embodiment analyte binding may occur with signaling aptamer (signaling aptamer having redox tag), and binding of analyte to signaling aptamer may serve to release signaling aptamer from anchor aptamer (such as by change in conformation of signaling aptamer).

It will be recognized that the device of the embodiment of FIG. 7 has a plurality of aptamers—and thus includes a plurality of signaling aptamers 772, and a plurality of anchor aptamers 774. As described above, each anchor aptamer of the plurality of anchor aptamers is adapted to bind to analyte. In one embodiment, each signaling aptamer of a majority of the plurality of signaling aptamers is bound to a respective anchor aptamer when a majority of anchor aptamers are not bound to any analyte. (This may occur, for example, prior to the introduction of any analyte.) Once analyte is introduced (such as when a sample fluid is introduced into the device—e.g., by being introduced into the sensor fluid of the device), at least a subset of anchor aptamers from the plurality of anchor aptamers then binds to analyte. When this occurs, a subset of signaling aptamers (from the total plurality of aptamers) dissociates from the anchor aptamers—and the redox tag becomes more available for electron transfer with the electrode.

Figure 8:
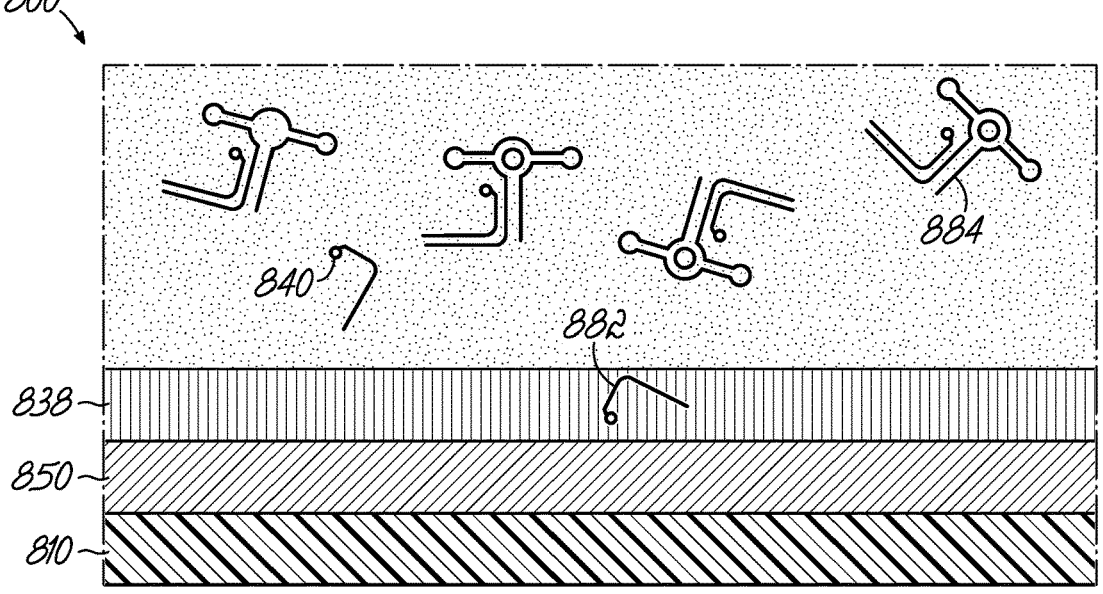
FIG. 8 is a schematic of yet another embodiment of a device in accordance with principles of the present invention.

With reference to FIG. 8, where like numerals refer to like features, another embodiment in accordance with aspects of the present invention is shown. As can be seen in FIG. 8, a portion of a device 800 is shown, and includes a substrate 810, at least one electrode 850, a membrane 838, a sensor fluid 18, a plurality of aptamers having redox tags 740 (free in the sensor fluid). Though not part of the device, analytes 19 are also depicted as present in the sensor fluid of the device. The aptamers/redox tags component of the embodiment of FIG. 8 is similar to that shown in FIGS. 5C, 6C, and 7, and includes two aptamer portions: a signaling aptamer 882 and an anchor aptamer 884. A redox tag 840 is associated with (such as by being attached to) the signaling aptamer 882. The anchor aptamer 884 includes a portion that has affinity for, and thus can bind, analyte 19. The membrane 838 exhibits selective permeability based on size, charge, or at least one solute property, and is able to pass a signaling aptamer 882 but not a signaling aptamer that is attached to a larger anchor aptamer 884. Thus, the membrane 838 impacts the availability of the redox couple 840 to the electrode 850. For example, a signaling aptamer could have a radius of 3 nm/2 nm in folded/unfolded states and an anchor aptamer have 27/7 nm in folded/unfolded state, creating a difference in size of ~3-10×when a signaling aptamer is freed from an anchor aptamer. Nanofiltration membranes can provide is nM pore sizes, and ultrafiltration 10s to 100s nm pore sizes (PES, track-etch, and other materials), resulting in size selective permeability that would enable mainly only the signaling aptamer 882 to penetrate the hydrogel or membrane 838.

And so, still referring to FIG. 8, when analyte 19 is not bound to the anchor aptamer 884, the signaling aptamer 882 remains associated with the anchor aptamer 884, and so the redox tag 840 on signaling aptamer 882 is less available (or not available) for electron transfer with the electrode 850 (because the signaling aptamer 882 will be unable to cross membrane 838 due to being complexed with anchor aptamer 884). However, once the anchor aptamer 884 binds to analyte 19, the signaling aptamer 882 is released from anchor aptamer 884 and is able to pass through membrane 838, resulting in the redox tag 840 becoming available for electron transfer with the electrode 850. Further, while the embodiment shown in FIG. 8 depicts analyte 19 binding to anchor aptamer 884 and redox tag 840 on signaling aptamer 882, in an alternate embodiment analyte binding may occur with signaling aptamer (signaling aptamer having redox tag), and binding of analyte to signaling aptamer may serve to release signaling aptamer from anchor aptamer (such as by change in conformation of signaling aptamer).

Figures 9, 10:
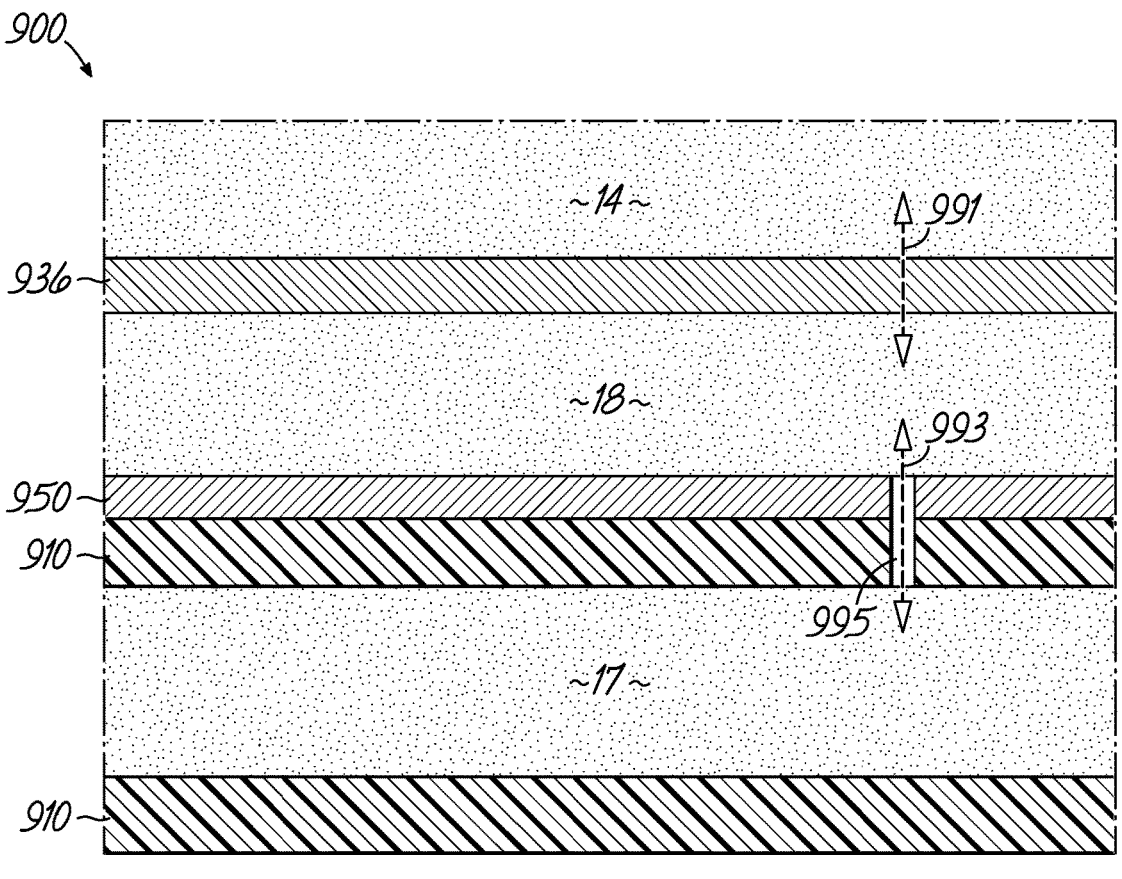
FIG. 9 is a schematic of yet another embodiment of a device in accordance with principles of the present invention.
FIG. 10 is a schematic of yet another embodiment in accordance with principles of the present invention including n adapter molecule and an aptamer with attached redox tag.

With reference to FIG. 9, where like numerals refer to like features, another embodiment in accordance with principles of the present invention is shown. In certain of the various embodiments discussed herein, a membrane is used to selectively allow passage of certain molecules and not of others. However, as no membrane is perfectly size selective, and as aptamers and redox tags can degrade over time, it may be advantageous to continually introduce a fresh supply of aptamers, signaling aptamers, and/or anchor aptamers or other solutes that increase performance of the sensor or improve longevity of the sensor (e.g. nuclease inhibitors, for example). Thus, as shown in FIG. 9, a portion of a device 900 includes substrates 910, at least one electrode 950, a membrane 936, a sample fluid 14, a sensor fluid 18, and a reservoir fluid 17. The membrane 936 exhibits mass flow represented at reference numeral 991, and the device also includes a diffusion restrictive feature 935 (such as a pinhole or membrane) with a mass flow represented at reference numeral 993.

As a nonlimiting example of that shown in FIG. 9, consider a 0.2 kDa dialysis membrane for membrane 936 and assume the aptamers are 10-100×larger than the solute to be detected (e.g. phenylalanine, cortisol, etc.). Assume the system is designed such that the volume of reservoir fluid 17 is at least one of 2×, 10×, 50×, or 250×greater than volume of sensor fluid 18 and that the mass flow 991 of aptamer is at least 2×, 10×, 50×, or 250×less than mass flow of aptamer 993, while the mass flow 991 of the analyte is at least 2×, 10×, 50×, or 250×greater than the mass flow of the analyte 993. As a result, the concentrations of analyte will be within at least 50%, 10%, 2%, or 0.4% of each other when comparing sample fluid 14 with sensor fluid 18, and the concentrations of aptamer will be within at least 50%, 10%, 2%, or 0.4% of each other when comparing sensor fluid 18 and reservoir fluid 17.

As a geometrical example, consider a membrane 936 with 0.2 cm² area and 10% porosity to the analyte, and a diffusion restrictive feature 935 that is a pinhole in materials 910 and 950 0.001 cm² in area and 0.001 cm in length. The mass transport for a small analyte through the membrane will be equivalent to 0.02 cm² area and the mass transport through the feature 935 0.001 cm², which is 20×different, satisfying the above stated criteria for design as shown in FIG. 9. As a result, both analyte and aptamer concentrations can be maintained for prolonged periods of times (days, weeks, months) even if aptamer is lost from the device or degraded over time. Aptamers could also degrade over time and their presence in the device and the presence of other contaminants such as nucleases or proteins could be problematic. For example, if signaling aptamers became cleaved and their molecular weight decreased, they could give a false higher reading of signal in embodiments of the present invention. With membrane protection of the sensor fluid from the sample fluid, most degradation or contamination modes will be very slow, such that the reservoir may also act as a waste removal element.

With further reference to FIG. 10, where like numerals refer to like features, another embodiment in accordance with principles of the present invention is shown. In particular, in the embodiment represented schematically in FIG. 10, a device (such as a device described in one of the embodiments above) includes at least one adapter molecule 980. This adapter molecule 980 is present in a device along with a plurality of aptamers (an example of such an aptamer 970 is shown in FIG. 10 having a redox tag 940 attached thereto).

As noted above, aptamers can interact with small molecules, but the ability to achieve high-affinity and selectivity of these interactions depends strongly on functional groups or epitopes displayed by the binding targets; and some classes of targets are particularly challenging: for example, monosaccharides have scarce functionalities such that no aptamers have been reported to recognize, let alone distinguish from each other, glucose and other hexoses. However, aptamers that differentiate low-epitope targets (such as glucose, fructose, or galactose) by forming ternary complexes with high-epitope organic adapters for monosaccharides have been reported. Although the use of such adapter molecules works well in a beaker for a rapid glucose assay (including optical aptamers, which do not contain a redox tag), such an approach will not work in a continuous biosensing format. This is because the adapter molecule 980, whatever the choice, cannot be immobilized like glucose oxidase can be (in an enzymatic sensor), or like the aptamer can be on an electrode (in certain affinity-based sensors). Rather, the adapter molecule 980 must be left free in solution. With devices of the present invention, (be they microneedles, indwelling, or implanted based sensors), the adapter molecule 980 must remain proximal to the sensor or the device will fail to work (or, at a minimum, performance of the device would be reduced and impaired if the adapter molecule diffuses away from the sensor). Furthermore, as described above, many adapter molecules 980 may be toxic or not approved for diffusion away from the sensor and into the body of the subject being tested. This tension between the competing facts that (1) adapter molecules cannot be allowed to diffuse away from the sensor, and (2) adapter molecules cannot be immobilized proximal to the sensor, has prevented development of devices including adapter molecules.

Various embodiments of the present invention, however, resolve this issue. Considering the issue raised by certain analytes, such as monosaccharides: Most monosaccharides are small, (e.g., glucose at ~180 Da; and other monosaccharides or metabolites, such as lactate, are generally less than 400 Da). However, suitable adapter molecules 980 are all typically greater than 400 Da in molecular weight. And so, in embodiments of the present invention, the differing sizes of adapter molecules as compared to target analytes can be used to resolve the drawbacks described above. In that regard, the device of an embodiment of the present invention may include a size-selective membrane that allows passage of target analyte, but does not allow passage of adapter molecule 980. In particular (in one embodiment), such a size-selective membrane can be placed inside the device between sample fluid and sensor fluid, allowing permeation of the analyte 19, such as glucose, but substantially blocking of the adapter molecule 980.

Thus, the adapter molecule 980 and aptamer 970 including redox tag 940 (as shown in FIG. 10) may be included in a device such as that shown schematically in FIG. 3, for example. FIG. 3 shows a device 300 (or at least a portion thereof) that includes an electrode 350 and at least one membrane 336 which separates a sample fluid 14 from a sensor fluid 18. In an embodiment including the components of FIG. 10, the sensor fluid 18 of that device 300 would contains a plurality of aptamers 970 having redox tags 940, and would contain a plurality of adapter molecules 980. In a non-limiting example, then, membrane (such as membrane 336) is able to pass small solutes (e.g., less than 200 Da) from the sample fluid to the sensor fluid—for example, an analyte such as glucose—but retains the adapter molecules 980 (e.g., greater than 400 Da) and also retains aptamers 970 (with redox tags 940) which are often greater that 10 kDa in molecular weight. This prevents the adapter molecule 980 from being lost into the body (where it could potentially harm), and keeps the adapter molecule 980 proximal to the sensor, without having to be immobilized to a surface. This also prevents the aptamer 970 with redox tag 940 from being lost into the body and thus no longer able be able to provide a measurement of the analyte. Non-limiting examples of such membranes include Nafion, hydrogels, polysulphone, polyester, or other suitable membranes used in nanofiltration or dialysis applications. The membrane could have a molecular weight cutoff, in different embodiments, that is less than 300 da, less than 400 Da, less than 600 Da, less than 1000 Da, or less than 5000 Da. The adapter molecule 980 could have a molecular weight, in different embodiments, that is at least one of greater than 300 Da, greater than 400 Da, greater than 600 Da, greater than 1000 Da, or greater than 5000 Da. Example adapter molecules or functional groups for glucose include monobromic and dibromic acids and cationic bromic acids. While the adapter molecule 980 must be able to be in solution (not bound to an electrode) the aptamer 970 can be free in solution or may be bound to an electrode (like aptamer 270 as illustrated in FIG. 2).

Although not described in detail herein, other steps which are readily interpreted from or incorporated along with the disclosed embodiments shall be included as part of the invention. The embodiments that have been described herein provide specific examples to portray inventive elements, but will not necessarily cover all possible embodiments commonly known to those skilled in the art.

What is claimed is:

1. A device for detecting the presence of, or measuring the concentration of amount of, at least one analyte in a sample fluid, the device comprising:

a sensor fluid;

a plurality of adapter molecules in the sensor fluid that are capable of binding to an analyte;

a plurality of aptamers in or exposed to the sensor fluid that are capable of binding to the analyte when analyte is bound to one or more adapter molecules of the plurality of adapter molecules;

at least one membrane in communication with the sensor fluid, wherein the membrane is permeable to the analyte but impermeable to the adapter molecule; and at least one detection component that is capable of detecting the binding of analyte by one or more of the plurality of aptamers.

2. The device of claim 1, wherein the detection component includes at least one electrode and one or more aptamers of the plurality of aptamers include a redox tag attached thereto.

3. The device of claim 1, wherein one or more aptamers of the plurality of aptamers are solutes in the sensor fluid.

4. The device of claim 2, wherein one or more aptamers of the plurality of aptamers are bound to the at least one electrode.

5. The device of claim 2, wherein detecting the binding occurs through a change in electron transfer from at least one redox tag.

6. The device of claim 5, wherein the change in electron transfer is chosen from one of greater than 5%, greater than 10%, greater than 20%, greater than 50%, greater than 100%, and greater than 200%.

7. The device of claim 2, further comprising a passivating layer on the at least one electrode.

8. The device of claim 7, wherein the passivating layer includes exogenous molecules.

9. The device of claim 8, wherein the exogenous molecules include mercaptohexanol.

10. The device of claim 7, wherein the passivating layer includes molecules that are endogenous to the sample fluid.

11. The device of claim 10, wherein a source of the endogenous molecules is the sample fluid.

12. The device of claim 1, wherein the detection component includes at least one optical source and at least one photodetector, and one or more aptamers of the plurality of aptamers include a fluorescent tag.

13. The device of claim 1, wherein said membrane has a molecular weight cutoff chosen from less than 300 Da, less than 400 Da, less than 600 Da, less than 1000 Da, less than 3 kDa, less than 5 kDa, less than 10 kDa, less than 30 kDa, less than 100 kDa, and less than 300 kDa.

14. The device of claim 1, wherein each adapter molecule of the plurality of adapter molecules has a molecular weight that is chosen from greater than 300 Da, greater than 400 Da, greater than 600 Da, greater than 1000 Da, greater than 3 kDa, greater than 5 kDa, greater than 10 kDa, greater than 30 kDa, greater than 100 kDa, and greater than 300 kDa.

15. The device of claim 1, wherein said analyte is glucose.

16. The device of claim 1, further comprising a housing having one or more interior chambers containing the sensor fluid, plurality of adapter molecules, plurality of aptamers, at least one membrane, and at least one detection component; and
wherein the housing is adapted to be placed outside of the body and the stratum-corneum of the skin of a subject.

17. The device of claim 1, further comprising a housing having one or more interior chambers containing the sensor fluid, plurality of adapter molecules, plurality of aptamers, at least one membrane, and at least one detection component; and
wherein the housing is at least a portion of an in-dwelling device.

18. The device of claim 17, further comprising one or more microneedles in fluid communication with the one or more interior chambers.

19. The device of claim 1, further comprising a housing having one or more interior chambers containing the sensor fluid, plurality of adapter molecules, plurality of aptamers, at least one membrane, and at least one detection component; and
wherein the housing is adapted to be implanted into a subject.

20. The device of claim 1, wherein the plurality of aptamers comprise a plurality of signaling aptamers and a plurality of anchor aptamers.

21. The device of claim 20, further comprising a plurality of redox tags bound to the plurality of signaling aptamers.

22. The device of claim 21, wherein the plurality of anchor aptamers are adapted to bind the analyte, and wherein each signaling aptamer of a majority of the plurality of signaling aptamers is bound to a respective anchor aptamer when a majority of anchor aptamers are not hound to any analyte.

23. The device of claim 21, wherein the plurality of anchor aptamers are adapted to bind the analyte, and wherein a subset of signaling aptamers dissociates from the anchor aptamers when at least a subset of anchor aptamers bind to any analyte.

24. The device of claim 23, wherein the detection component includes at least one electrode and the redox tag is more available for electron transfer with the at least one electrode when the subset of signaling aptamers dissociates from the anchor aptamers.

25. The device of claim 21, further comprising a poorly-mobile or non-mobile material disposed within the sensor fluid, and wherein one or more anchor aptamers of the plurality of anchor aptamers are bound to the poorly mobile or non-mobile material.

26. The device of claim 25, wherein the plurality of anchor aptamers are adapted to bind the analyte, and wherein a subset of signaling aptamers dissociates from the anchor aptamers when at least a subset of anchor aptamers bind to any analyte.

27. The device of claim 26, wherein each redox tag attached to a dissociated signal aptamer becomes more available to the electrode than when the signal aptamer was bound to an anchor aptamer.

28. The device of claim 21, further comprising a second membrane, the second membrane being permeable to a signaling aptamer, but not being permeable to an anchor aptamer or to a complex of a signaling aptamer with an anchor aptamer.

29. The device of claim 2, further comprising a plurality of quenchers, wherein each quencher of the plurality of quenchers is attached to an aptamer that also includes a redox tag.

30. The device of claim 29, wherein each redox tag and quencher on a common aptamer are brought into closer proximity with one another when the aptamer binds to analyte.

31. The device of claim 29, wherein the redox tag and quencher are the same molecule.

32. The device of claim 31, wherein the redox tag is active in monomer form, but when brought into proximity with the quencher forms a dimer.

33. The device of claim 2, wherein one or more aptamers of the plurality of aptamers includes a first redox tag and a second redox tag.

34. The device of claim 33, wherein the first redox tag and second redox tag on a common aptamer are brought into closer proximity with one another when the aptamer binds to analyte.

35. The device of claim 34, wherein electron transfer from the first redox tag or the second redox tag is altered due to a two-step mediated electron transfer process.

36. The device of claim 1, further comprising a hydrogel, wherein the sensor fluid including the plurality of aptamers is disposed within the hydrogel, one or more aptamers of the plurality of aptamers including a redox tag attached thereto.

37. The device of claim 36, wherein the detection component includes a first electrode and a second electrode.

38. The device of claim 36, wherein, when one or more aptamers of the plurality of aptamers binds analyte, the size of the one or more aptamers decreases.

39. The device of claim 38, wherein the decrease in size is due to a decrease in hydrodynamic radius.

40. The device of claim 1, further comprising at least one reservoir fluid.

41. The device of claim 40, further comprising a diffusion restrictive feature.

42. The device of claim 41, wherein the membrane exhibits a first mass flow between sample fluid and sensor fluid, and the diffusion restrictive feature exhibits a second mass flow between sensor fluid and reservoir fluid.

43. The device of claim 42, wherein the first mass flow is a mass flow of aptamer and the second mass flow is a mass flow of aptamer, and wherein the first mass flow is less than the second mass flow of aptamer by a factor chosen from at least 2×, at least 10×, at least 50×, and at least 250×.

44. The device of claim 43, wherein a concentration of the plurality of aptamers in the sensor fluid as compared to a concentration of the plurality of aptamers in the reservoir fluid will be within a percentage chosen from at least 50%, at least 10%, at least 2% and at least 0.4%.

45. The device of claim 42, wherein the first mass flow is a mass flow of analyte and the second mass flow is a mass flow of analyte, and wherein the first mass flow is greater than the second mass flow of aptamer by a factor chosen from at least 2×, at least 10×, at least 50×, and at least 250×.

46. The device of claim 45, wherein a concentration of the analyte in the sample fluid as compared to a concentration of the analyte in the sensor fluid will be within a percentage chosen from at least 50%, at least 10%, at least 2% and at least 0.4%.

47. The device of claim 40, wherein the reservoir fluid is a repository for waste material that enters the reservoir fluid from the sensor fluid.

* * * * *